(12) United States Patent
Wanner et al.

(10) Patent No.: US 10,557,859 B2
(45) Date of Patent: Feb. 11, 2020

(54) ASTROCYTE TRAUMATOME AND NEUROTRAUMA BIOMARKERS

(71) Applicant: THE REGENTS OF THE UNIVERSITY OF CALIFORNIA, Oakland, CA (US)

(72) Inventors: Ina-Beate Wanner, Topanga, CA (US); Joseph A. Loo, Encino, CA (US)

(73) Assignee: THE REGENTS OF THE UNIVERSITY OF CALIFORNIA, Oakland, CA (US)

(*) Notice: Subject to any disclaimer, the term of this patent is extended or adjusted under 35 U.S.C. 154(b) by 0 days.

(21) Appl. No.: 15/570,982

(22) PCT Filed: May 5, 2016

(86) PCT No.: PCT/US2016/031043
§ 371 (c)(1),
(2) Date: Oct. 31, 2017

(87) PCT Pub. No.: WO2016/179426
PCT Pub. Date: Nov. 10, 2016

(65) Prior Publication Data
US 2018/0364259 A1 Dec. 20, 2018

Related U.S. Application Data

(60) Provisional application No. 62/157,389, filed on May 5, 2015.

(51) Int. Cl.
| | | |
|---|---|---|
| G01N 33/53 | (2006.01) | |
| G01N 33/566 | (2006.01) | |
| A61K 38/00 | (2006.01) | |
| G01N 33/68 | (2006.01) | |
| G01N 33/577 | (2006.01) | |

(52) U.S. Cl.
CPC ....... *G01N 33/6896* (2013.01); *G01N 33/577* (2013.01); *G01N 33/6848* (2013.01); *C12Y 201/01259* (2015.07); *G01N 2800/2871* (2013.01); *G01N 2800/40* (2013.01); *G01N 2800/52* (2013.01)

(58) Field of Classification Search
None
See application file for complete search history.

(56) References Cited

U.S. PATENT DOCUMENTS

| | | |
|---|---|---|
| 2011/0082203 A1 | 4/2011 | Wang |
| 2011/0177974 A1 | 7/2011 | Wang |
| 2014/0045713 A1 | 2/2014 | Everett |

FOREIGN PATENT DOCUMENTS

| | | |
|---|---|---|
| CN | CN1031118698 A | 5/2013 |
| WO | WO2011147981 A2 | 12/2011 |

OTHER PUBLICATIONS

Meco C, Arrer E, Oberascher G. 2007. Efficacy of cerebrospinal fluid fistula repair: Sensitive quality control using the beta-trace protein test. Am J Rhinol 21:729-736.
Mouser PE, Head E, Ha KH, Rohn TT. 2006. Caspase-mediated cleavage of glial fibrillary acidic protein within degenerating astrocytes of the Alzheimer's disease brain. Am J Pathol 168:936-46.
Mu J, Yang Y, Chen J, Cheng K, Li Q, Wei Y, Zhu D, Shao W, Zheng P, Xie P. 2015. Elevated host lipid metabolism revealed by iTRAQ-based quantitative proteomic analysis of cerebrospinal fluid of tuberculous meningitis patients. Biochem Biophys Res Commun 466:689-95.
Newcombe J, Woodroofe MN, Cuzner ML. 1986. Distribution of glial fibrillary acidic protein in gliosed human white matter. J Neurochem 47:1713-9.
Okonkwo DO, Yue JK, Puccio AM, Panczykowski DM, Inoue T, McMahon PJ, Sorani MD, Yuh EL, Lingsma HF, Maas Al and others. 2013. GFAP-BDP as an acute diagnostic marker in traumatic brain injury: results from the prospective transforming research and clinical knowledge in traumatic brain injury study. J Neurotrauma 30:1490-7.
Osman I, Gaillard O, Meillet D, Bordas-Fonfrede M, Gervais A, Schuller E, Delattre J, Legrand A. 1995. A sensitive time-resolved immunofluorometric assay for the measurement of apolipoprotein B in cerebrospinal fluid. Application to multiple sclerosis and other neurological diseases. Eur J Clin Chem Clin Biochem 33:53-8.
Osuna E, Perez-Carceles MD, Luna A, Pounder DJ. 1992. Efficacy of cerebro-spinal fluid biochemistry in the diagnosis of brain insult. Forensic Sci Int 52(2):193-8.
Jahari DR, Gu YJ, van Oeveren W, El-Essawi A, Harringer W, Brouwer RM. 2013. Effect of minimized perfusion circuit on brain injury markers carnosinase and brain-type fatty binding protein in coronary artery bypass grafting patients. Artif Organs 37:128-35.
Papa L, Lewis LM, Falk JL, Zhang Z, Silvestri S, Giordano P, Brophy GM, Demery JA, Dixit NK, Ferguson I and others. 2012. Elevated levels of serum glial fibrillary acidic protein breakdown products in mild and moderate traumatic brain injury are associated with intracranial lesions and neurosurgical intervention. Ann Emerg Med 59:471-83.

(Continued)

*Primary Examiner* — Olga N Chernyshev
(74) *Attorney, Agent, or Firm* — Karen S. Canady; canady + lortz LLP

(57) ABSTRACT

A method for detection or monitoring status of traumatic brain injury (TBI) or spinal cord injury (SCI) in a subject is provided. In one embodiment, the method comprises contacting a specimen of bodily fluid obtained from the subject with reagents for assaying for a marker of TBI selected from aldolase C (ALDOC) and brain lipid binding protein (BLBP), or a trauma-specific break down product (BDP) of ALDOC or BLBP. The method further comprises measuring the amount of marker present in the specimen as compared to a control sample, and determining the presence of TBI or SCI when an elevated amount of marker is present in the specimen compared to the control sample. The method can comprises measuring the amount of glutamine synthetase (GS), astrocytic phosphoprotein PEA-15 (PEA15), αB-crystallin (CRYAB/HSP27), a cleavage product of ALDOC, GS, PEA15, or CRYAB, or a combination of two or more thereof.

25 Claims, 22 Drawing Sheets
Specification includes a Sequence Listing.

(56) References Cited

OTHER PUBLICATIONS

Pelinka LE, Kroepfl A, Leixnering M, Buchinger W, Raabe A, Redl H. 2004a. GFAP versus S100B in serum after traumatic brain injury: relationship to brain damage and outcome. J Neurotrauma 21:1553-61.

Pelinka LE, Kroepfl A, Schmidhammer R, Krenn M, Buchinger W, Redl H, Raabe A. 2004b. Glial fibrillary acidic Protein in serum after traumatic brain injury and multiple trauma. J Trauma 57:1006-12.

Pelsers MM, Hanhoff T, Van der Voort D, Arts B, Peters M, Ponds R, Honig A, Rudzinski W, Spener F, de Kruijk JR and others. 2004. Brain- and heart-type fatty acid-binding proteins in the brain: tissue distribution and clinical utility. Clin Chem 50:1568-75.

Reiber H, Walther K, Althaus H. 2003. Beta-trace protein as sensitive marker for CSF rhinorhea and CSF otorhea. Acta Neurol Scand 108:359-62.

Rivett AJ. 1985. Preferential degradation of the oxidatively modified form of glutamine synthetase by intracellular mammalian proteases. J Biol Chem 260:300-5.

Rohn TT, Catlin LW, Poon WW. 2013. Caspase-cleaved glial fibrillary acidic protein within cerebellar white matter of the Alzheimer's disease brain. Int J Clin Exp Pathol 6:41-8.

Shen S, Loo RR, Wanner IB, Loo J. Addressing the needs of traumatic brain injury with clinical proteomics. Clin Proteomics. Mar. 28, 2014;11(1):11. doi: 10.1186/1559-0275-11-11.

Stoevring B, Frederiksen JL, Christiansen M. 2007. CRYAB promoter polymorphisms: influence on multiple sclerosis susceptibility and clinical presentation. Clin Chim Acta 375:57-62.

Teunissen CE, Veerhuis R, De Vente J, Verhey FR, Vreeling F, van Boxtel MP, Glatz JF, Pelsers MA. 2011. Brain-specific fatty acid-binding protein is elevated in serum of patients with dementia-related diseases. Eur J Neurol 18:865-71.

Timmer NM, Herbert MK, Claassen JA, Kuiperij HB, Verbeek MM. 2015. Total glutamine synthetase levels in cerebrospinal fluid of Alzheimer's disease patients are unchanged. Neurobiol Aging 36:1271-3.

Vadakkan KI, Mammen T, Wadhwa VS. 2015. Sum of two catalytic activities of the glutamine synthetase enzyme is a blood biomarker for stroke and is optimized for a rapid diagnostic test. Int J Stroke 10:E1-2.

Vazquez MD, Sanchez-Rodriguez F, Osuna E, Diaz J, Cox DE, Perez-Carceles MD, Martinez P, Luna A, Pounder DJ. 1995. Creatine kinase BB and neuron-specific enolase in cerebrospinal fluid in the diagnosis of brain insult. Am J Forensic Med Pathol 16:210-4.

Vermeiren Y, Le Bastard N, Clark CM, Engelborghs S, De Deyn pp. 2011. Serum glutamine synthetase has no value as a diagnostic biomarker for Alzheimer's disease. Neurochem Res 36:1858-62.

Wanner Ina B., et al., Profiling the Injury Signature of Astrocytes for New Neurotrauma Biomarkers. Abstract from The 30th Annual National Neurotrauma Symposium.Jul. 22-25, 2012. Phoenix Arizona. p. A-61.

Wanner Ina B., et al., Profiling the Injury Signature of Astrocytes for New Neurotrauma Biomarkers. Poster Presented 2012. Phoenix Arizona.

Wijman, C.A.C., et al., Research and Technology in Neurocritical Care. Neurocrit Care. Feb. 2012 ; 16(1): 42-54.

Wunderlich MT, Hanhoff T, Goertler M, Spener F, Glatz JF, Wallesch CW, Pelsers MM. 2005. Release of brain-type and heart-type fatty acid-binding proteins in serum after acute ischaemic stroke. J Neurol 252:718-24.

Yan X, Liu T, Yang S, Ding Q, Liu Y, Zhang X, Que H, Wei K, Luo Z, Liu S. 2009. Proteomic profiling of the insoluble pellets of the transected rat spinal cord. J Neurotrauma 26:179-93.

Yang Z, Wang KK 2015. Glial fibrillary acidic protein: from intermediate filament assembly and gliosis to neurobiomarker. Trends Neurosci 38:364-374.

Zhang, Zhiqun, et al., Human Traumatic Brain Injury Induces Autoantibody Response against Glial Fibrillary Acidic Protein and Its Breakdown Products. PLoS ONE 9(3): e92698.

Zhao X, Ahram A, Berman RF, Muizelaar JP, Lyeth BG. 2003. Early loss of astrocytes after experimental traumatic brain injury. Glia 44:140-52.

Zoltewicz JS, Scharf D, Yang B, Chawla A, Newsom KJ, Fang L. 2012. Characterization of Antibodies that Detect Human GFAP after Traumatic Brain Injury. Biomark Insights 7:71-9.

International Search Report and Written Opinion for PCT/US2016/031043 (WO16179426 Published Nov. 10, 2016).

Arrer E, Meco C, Oberascher G, Piotrowski W, Albegger K, Patsch W. 2002. beta-Trace protein as a marker for cerebrospinal fluid rhinorrhea. Clin Chem 48:939-41.

Asaka M, Kimura T, Nishikawa S, Saitoh M, Miyazaki T, Takatori T, Alpert E. 1990. Serum aldolase isozyme levels in Patients with cerebrovascular diseases. Am J Med Sci 300(5):291-5.

Bachmann-Harildstad G, Stenklev NC, Myrvoll E, Jablonski G, Klingenberg O. 2011. beta-trace protein as a diagnostic marker for perilymphatic fluid fistula: a prospective controlled pilot study to test a sample collection technique. Otol Neurotol 32:7-10.

Bachmann-Harildstad G. 2008. Diagnostic values of beta-2 transferrin and beta-trace protein as markers for cerebrospinal fluid fistula. Rhinology 46:82-5.

Barzo, P, et al. Magnetic resonance imaging-monitored acute blood-brain barrier changes in experimental traumatic brain injury. J Neurosurg 85:1113-1121, 1996.

Bourguignat A, Ferard G, Jung G, Klumpp T, Metais P. 1983. Multivariate analysis of plasma enzyme profiles in severe head injury. Clin Chem 29:107-9.

Brettschneider J, Riepe MW, Petereit HF, Ludolph AC, Tumani H. 2004. Meningeal derived cerebrospinal fluid proteins in different forms of dementia: is a meningopathy involved in normal pressure hydrocephalus? J Neurol Neurosurg Psychiatry 75:1614-6.

Buki, A. et al. (2015) Minor and Repetitive Head Injury. In: Schramm J. (eds) Advances and Technical Standards in Neurosurgery. Advances and Technical Standards in Neurosurgery, vol. 42. Springer, Cham.

Chang RY, Etheridge N, Dodd PR, Nouwens AS. 2014. Targeted quantitative analysis of synaptic proteins in Alzheimer's disease brain. Neurochem Int 75:66-75.

Chen MH, Hagemann TL, Quinlan RA, Messing A, Perng MD. 2013. Caspase cleavage of GFAP produces an assembly-compromised proteolytic fragment that promotes filament aggregation. ASN Neuro 5:e00125.

Ding B Xi Y, Gao M, Li Z, Xu C, Fan S, He W. 2014. Gene expression profiles of entorhinal cortex in Alzheimer's disease. Am J Alzheimers Dis Other Demen 29(6):526-32.

Feala, Jacob D., et al., Systems Biology Approaches for Discovering Biomarkers for Traumatic Brain Injury Journal of Neurotrauma. Jul. 2013, 30(13): 1101-1116.

Florez G, Cabeza A, Gonzalez JM, Garcia J, Ucar S. 1976. Changes in serum and cerebrospinal fluid enzyme activity after head injury. Acta Neurochir (Wien) 35(1-3)3-11.

Gao WM, Chadha MS, Berger RP, Omenn GS, Allen DL, Pisano M, Adelson PD, Clark RS, Jenkins LW, Kochanek PM. 2007. A gel-based proteomic comparison of human cerebrospinal fluid between inflicted and non-inflicted pediatric traumatic brain injury. J Neurotrauma 24:43-53.

Hausdoerfer J, Heller W, Schinkmann L. 1975. Biochemical and biophysical changes in guinea pigs after acute head injury. Resuscitation 4(2):77-86.

Hicks, RR, et al. Mild Experimental Brain Injury in the Rat Induces Cognitive Deficits Associated with Regional Neuronal Loss in the Hippocampus. 1993 J of Neurotrauma 10(4):405-414.

Ichkova, Aleksandra and Badaut, Jerome. New biomarker stars for traumatic brain injury. Journal of Cerebral Blood Flow & Metabolism. 2017, vol. 37(10) 3276-3277.

Jung G, Morel J, Bourguignat A, Ferard G. 1983. Modifications of plasma enzyme activities after severe head injury; evaluation of prognosis using multivariate methods. Clin Chim Acta 127(3):365-71.

Kay AD, Day SP, Nicoll JA, Packard CJ, Caslake MJ. 2003. Remodelling of cerebrospinal fluid lipoproteins after subarachnoid hemorrhage. Atherosclerosis 170:141-6.

(56) References Cited

OTHER PUBLICATIONS

Ke K, Li L, Rui Y, Zheng H, Tan X, Xu W, Cao J, Xu J, Cui G, Xu G and others. 2013. Increased expression of small seat shock protein alphaB-crystallin after intracerebral hemorrhage in adult rats. J Mol Neurosci 51:159-69.

Klun B. 1974. Spinal fluid and blood serum enzyme activity in brain injuries. J Neurosurg 41(2):224-8.

Koh, DW, Dawson TM, Dawson VL. Mediation of cell death by poly(ADP-ribose) polymerase-1. Pharmacol Res. Jul. 2005;52(1):5-14.

Koh, L., et al. Development of cerebrospinal fluid absorption sites in the pig and rat: connections between the subarachnoid space and lymphatic vessels in the olfactory turbinates. Anat Embryol (Berl). Aug. 2006;211(4):335-44. Epub Mar. 10, 2006.

Koh, Phil-Ok, Melatonin prevents down-regulation of astrocytic phosphoprotein PEA-15 in ischemic brain injury. J of Pineal Research, vol. 51, Issue 4, Nov. 2011, pp. 381-386.

Koh, Phil-Ok. 2012a. Ferulic acid prevents the cerebral ischemic injury-induced decreases of astrocytic phosphoprotein PEA-15 and its two phosphorylated forms. Neurosci Lett 511:101-5.

Koh, Phil-Ok. 2012b. Nicotinamide attenuates the decrease of astrocytic phosphoprotein PEA-15 in focal cerebral schemic injury. J Vet Med Sci 74:377-80.

Koh, Phil-Ok. Gingko biloba Extract (EGb 761) Attenuates the Focal Cerebral Ischemic Injury-Induced Decrease in Astrocytic Phosphoprotein PEA-15 Levels. The American Journal of Chinese Medicine, vol. 39, No. 5, 971-979. DOI: 10.1142/S0192415X11009342.

Korn, Akira, et al. Focal Cortical Dysfunction and Blood-Brain Barrier Disruption in Patients With Postconcussion Syndrome. Journal of Clinical Neurophysiology. vol. 22, No. 1, Feb. 2005. pp. 1-9.

Kulhanek, V. Die Aldolaseaktivaet in Der Cerebrospinalen Fluessigkeit Nach Intrakranialen Verletzungen. Monatsschrift fur Unfallheilkunde, Versicherungs-, Versorgungs- und Verkehrsmedizin. 1963. 365-9.

Lee A, Lingwood BE, Bjorkman ST, Miller SM, Poronnik P, Barnett NL, Colditz P, Pow DV. 2010. Rapid loss of glutamine synthetase from astrocytes in response to hypoxia: implications for excitotoxicity. J Chem Neuroanat 39:211-20.

Linke S, Goertz P, Baader SL, Gieselmann V, Siebler M, Junghans U, Kappler J. 2006. Aldolase C/zebrin II is released to the extracellular space after stroke and inhibits the network activity of cortical neurons. Neurochem Res 31 (11)1297-303.

Lubieniecka JM, Streijger F, Lee JH, Stoynov N, Liu J, Mottus R, Pfeifer T, Kwon BK, Coorssen JR, Foster LJ and others. 2011. Biomarkers for severity of spinal cord injury in the cerebrospinal fluid of rats. PLoS One 6:e19247.

Lumpkins KM, Bochicchio GV, Keledjian K, Simard JM, McCunn M, Scalea T. 2008. Glial fibrillary acidic protein is highly correlated with brain injury. J Trauma 65:778-82; discussion 782-4.

Martinez A, Carmona M, Portero-Otin M, Naudi A, Pamplona R, Ferrer I. 2008. Type-dependent oxidative damage in frontotemporal lobar degeneration: cortical astrocytes are targets of oxidative damage. J Neuropathol Exp Neurol 67:1122-36.

Mase M, Yamada K, Iwata A, Matsumoto T, Seiki K, Oda H, Urade Y. 1999. Acute and transient increase of lipocalin-type prostaglandin D synthase (beta-trace) level in cerebrospinal fluid of patients with aneurysmal subarachnoid hemorrhage. Neurosci Lett 270:188-90.

Mase M, Yamada K, Shimazu N, Seiki K, Oda H, Nakau H, Inui T, Li W, Eguchi N, Urade Y. 2003. Lipocalin-type prostaglandin D synthase (beta-trace) in cerebrospinal fluid: a useful marker for the diagnosis of normal pressure hydrocephalus. Neurosci Res 47:455-9.

Mathiisen TM, et al. The perivascular astroglial sheath provides a complete covering of the brain microvessels: an electron microscopic 3D reconstruction. Glia. Jul. 2010;58(9):1094-103. doi: 10.1002/glia.20990.

McMahon PJ, Panczykowski DM, Yue JK, Puccio AM, Inoue T, Sorani MD, Lingsma HF, Maas AL, Valadka AB, Yuh EL and others. 2015. Measurement of the glial fibrillary acidic protein and its breakdown products GFAP-BDP biomarker for the detection of traumatic brain injury compared to computed tomography and magnetic resonance imaging. J Neurotrauma 32:527-33.

Meco C, Oberascher G, Arrer E, Moser G, Albegger K. 2003. Beta-trace protein test: new guidelines for the reliable diagnosis of cerebrospinal fluid fistula. Otolaryngol Head Neck Surg 129:508-17.

Hulscher, Jan B., et al. "The Diagnostic Value of Brain-Fatty Acid Binding Protein in Traumatic Brain Injury." Journal of Neurotrauma, 31(4), p. 411. vol. 31 Issue 4: Feb. 10, 2014. http://doi.org/10.1089/neu.2013.3099.

Extended European Search Report from corresponding EP Application 16790108.1 dated Aug. 8, 2018.

First Office Action from corresponding CN Application 201680032940.6 reported by foreign associate dated Mar. 1, 2019; first received by Applicants' representative on Apr. 4, 2019 (Machine Translation provided).

Yang, Xinyu, et al., Expressive proteomics profile changes of injured human brain cortex due to acute brain trauma, Brain Injury, vol. 23, No. 10, pp. 830-840, Sep. 2009.

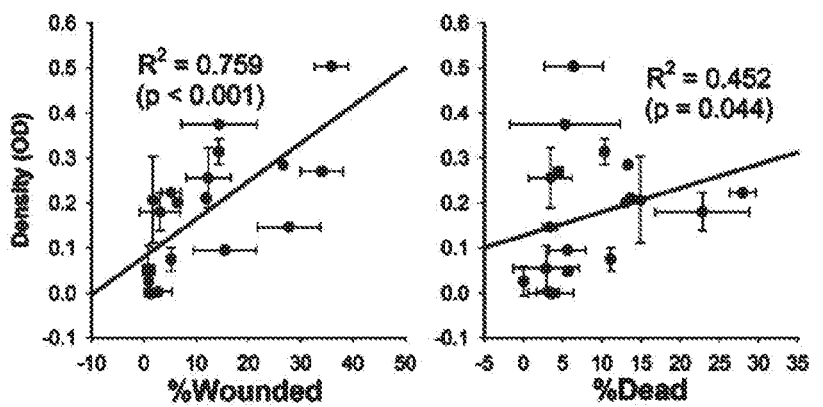
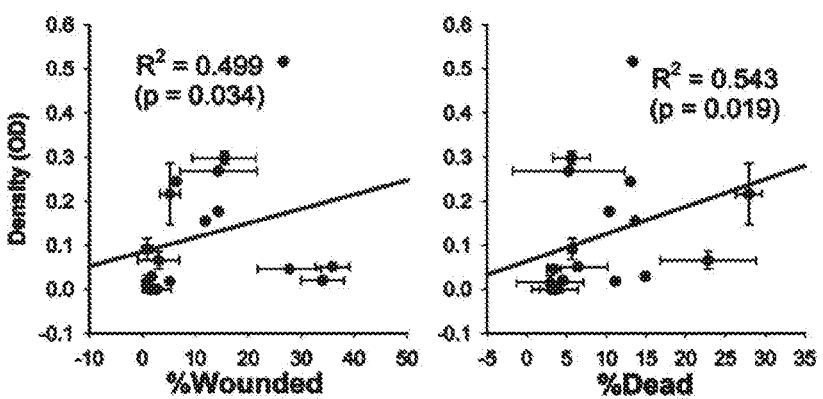
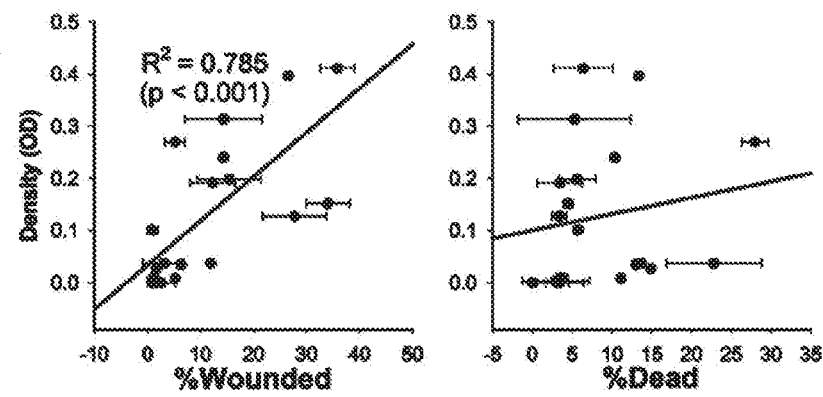
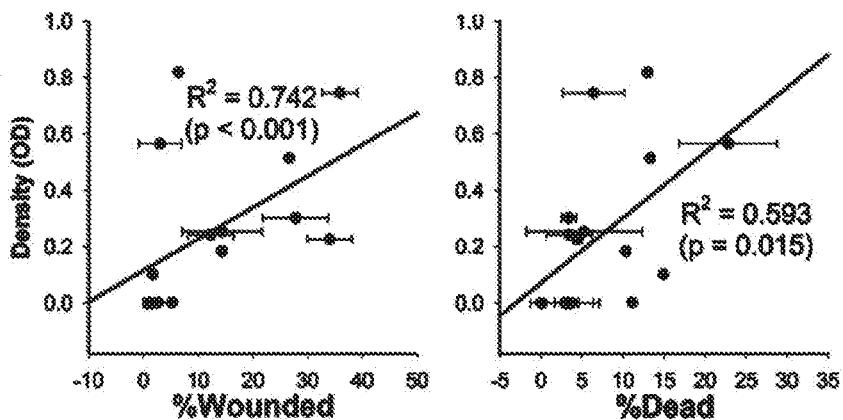
FIGURE 4A

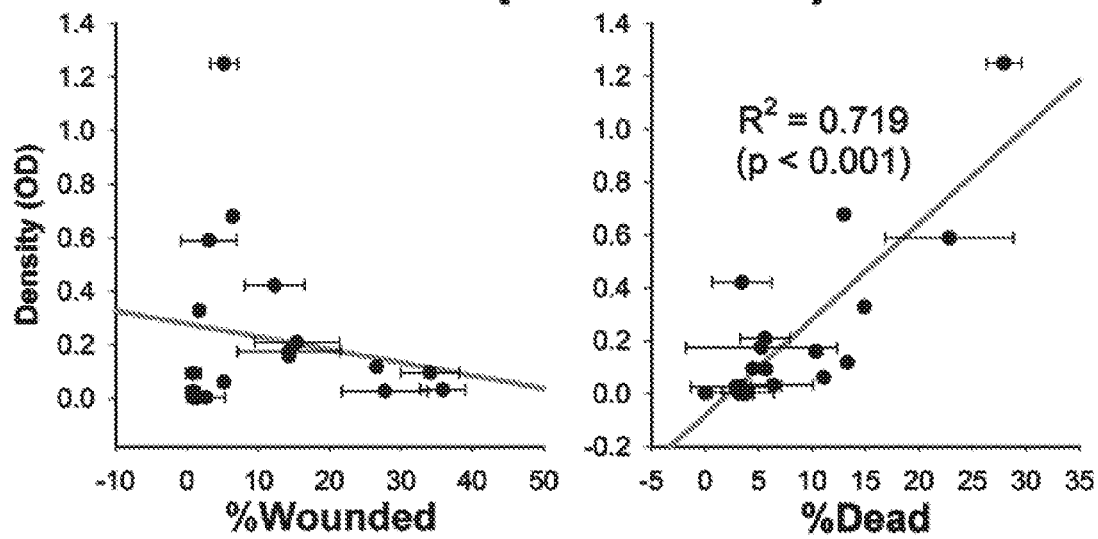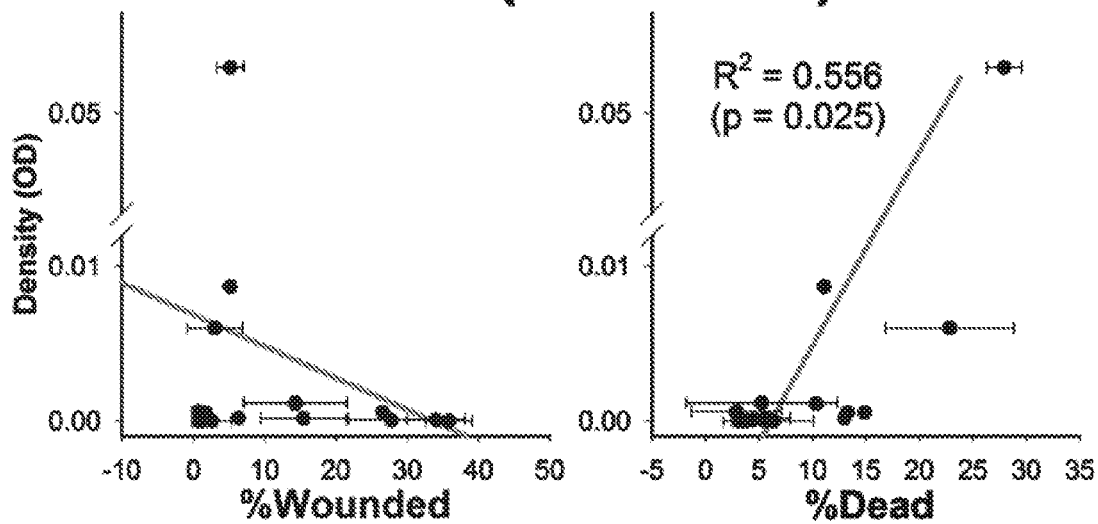
FIGURE 4B

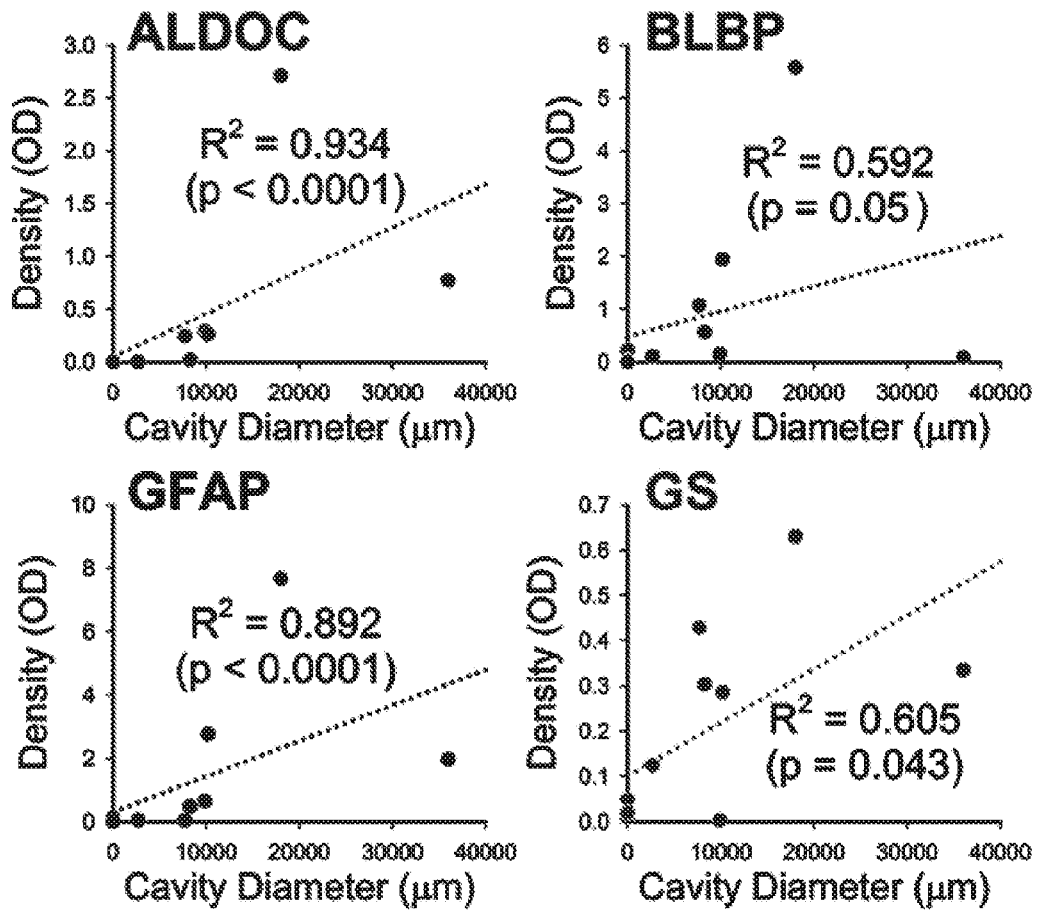
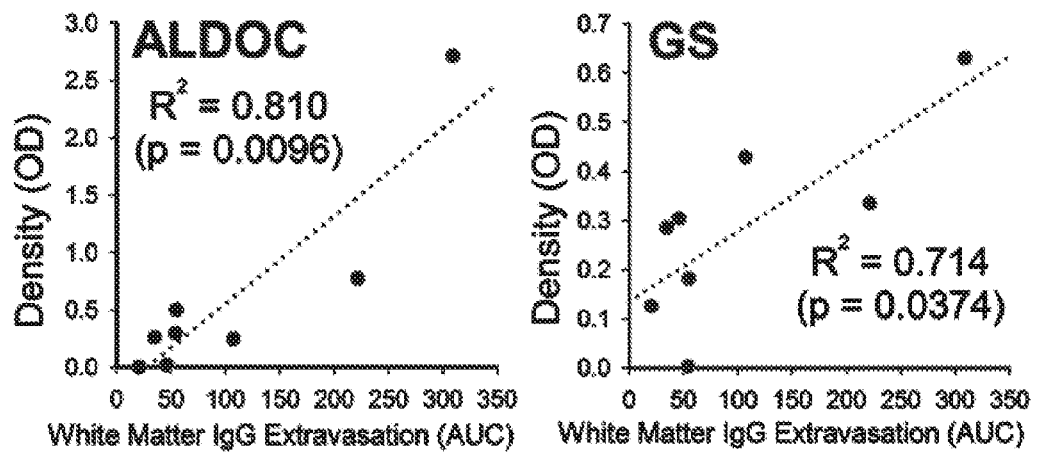
FIGURE 11

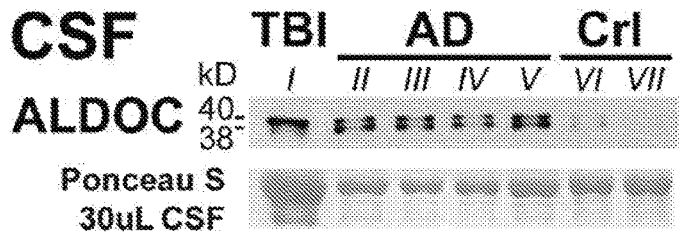
FIGURE 21
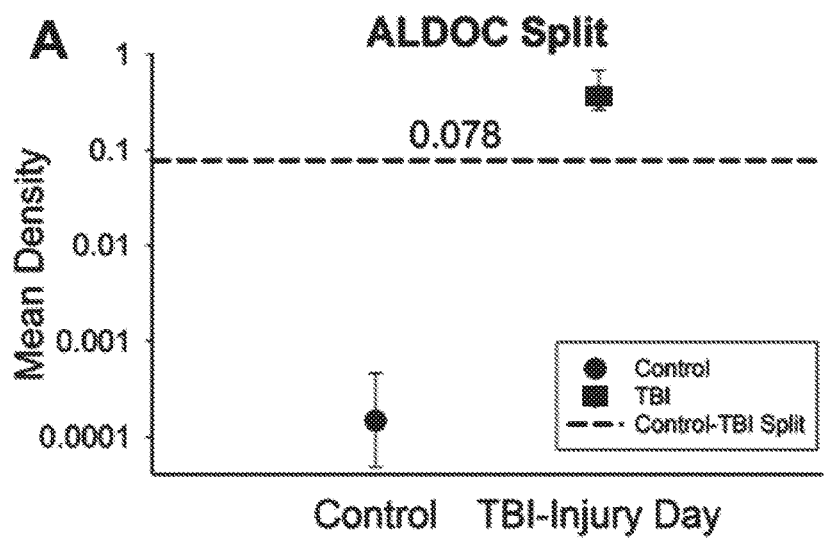
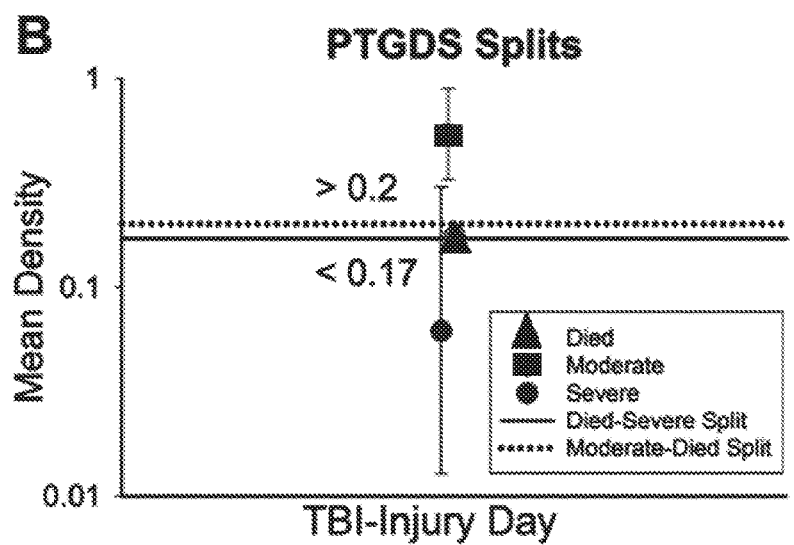
FIGURE 22

ASTROCYTE TRAUMATOME AND NEUROTRAUMA BIOMARKERS

This application claims benefit of U.S. provisional patent application No. 62/157,389, filed May 5, 2015, the entire contents of which are incorporated by reference into this application.

ACKNOWLEDGEMENT OF GOVERNMENT SUPPORT

This invention was made with government support under Grant No. NS072606, awarded by the National Institutes of Health, Grant Number W81XWH-13-2-0047, awarded by the Department of Defence. The government has certain rights in the invention.

REFERENCE TO A SEQUENCE LISTING SUBMITTED VIA EFS-WEB

The content of the ASCII text file of the sequence listing named "UCLA217_SL" which is 3 kb in size was created on May 5, 2016, and electronically submitted via EFS-Web herewith the application is incorporated herein by reference in its entirety.

TECHNICAL FIELD OF THE INVENTION

The present invention relates to compositions of matter, including antibodies, probes, kits and related materials, and their use for detection, early prediction of severity and outcome, monitoring of progression and of treatment of neurotrauma, including traumatic brain injury (TBI), mild TBI (concussion) and traumatic spinal cord injury (SCI) and their distinction from chronic neurodegenerative diseases.

BACKGROUND OF THE INVENTION

Each year, 1.7 million individuals sustain a TBI in the US. Between 1.6 and 3.8 million often unreported concussions occur annually, making TBI a silent epidemic of great significance. An additional one million patients are evaluated for spinal injuries every year in the US emergency departments, with 2-3 percent thereof suffering spinal cord injury. Life-saving treatment decisions for neurotrauma patients require rapid diagnosis and repeated accurate risk assessment due to evolving injury progression, as a brain trauma victim's condition typically changes each day after a TBI. Assessing moderate and severe traumatic brain and spinal cord injured patients is critical for safe urgent care, monitoring injury evolution to be ready for responding to secondary adverse events and for predicting outcome that is an early evaluation of the recovery potential for neurotrauma patients. Neurotrauma patient assessment is challenged by a broad heterogeneity in severity among patients. Identifying individual concussion victims at risk of complications, these are mild TBI patients with persistent symptoms or positive CAT scan finding, is a priority for urgent care responders as well as sports and military arena operations. Infants, children and juvenile brain injuries comprise the leading cause of death and disability in children worldwide, yet the diagnosis is challenging because signs and symptoms of TBI are absent or overlap with common childhood illnesses. Since the developing brain is more sensitive to the ionizing radiation of CAT scanning, it is imperative to reduce unnecessary CT scans by providing objective biomarker testing. In addition to the youth, the elderly are a common target group for TBI due to falls, making it desirable to distinguish TBI biomarker signals from chronic neurodegenerative marker profiles.

Diagnosis and monitoring of TBI victims is critical for assessing severity of brain disturbance and assessing the risk level accurately to respond with the appropriate preventative care. For severe TBI patients, timely surgical intervention could be life-saving. For mild TBI patients, the identification of concussion patients at risk for developing chronic pain and cognitive or psychological deficits will help to provide treatment options, guidance in coping strategies and prevent exposing the recovering brain to a second impact. Current severity evaluations rely mainly on depth and duration of coma using the Glasgow Coma Scale, which varies daily with the patient's progressive injury course and is subject to medications that may be needed to maintain a coma (Iankova, 2006). Mild TBI is evaluated by time of unconsciousness, cognitive or psychological and pain symptoms that are subjective and may be motivationally influenced. Neuroimaging tools, especially advanced modalities, are difficult to be repeatedly administered for intensive care patients and have diverse readout values that lack standardization, are not everywhere available, and are of limited use for mild TBI and pediatric patients.

Measuring blood levels of surrogate chemical biomarkers can provide a simpler, objective and more easily standardized tool as a diagnostic starting point to classify risk and needs for TBI patients. Neurotrauma biomarkers should be acutely released from traumatized brain cells, be brain and mechanical trauma specific, readily pass the blood-brain barrier and show no or consistent low levels in healthy subjects.

Currently, there is no sensitive, objective, standardized diagnostic test in clinical use for concussion patients, who are the majority of TBI patients, nor for pediatric patients with suspected TBI. These are both target populations particularly in need of objective risk assessment to prevent repeated hits putting the vulnerable brain at risk for suffering lasting brain damage. Intensive care unit head trauma patients are another target group who can benefit from repeated noninvasive blood sample analysis for monitoring, instead of, or supplementing time and cost consuming imaging because trauma progression is known for secondary deterioration on consecutive post-injury days that might require informed intervention. In addition, there remains a need for repeated biofluid sample analysis of brain injury biomarkers to determine short-term post-acute severity assessment and to determine efficacy of drug or other treatment paradigms administered to TBI patients.

SUMMARY OF THE INVENTION

The invention meets these needs and others, by providing a method for detection or monitoring status of traumatic brain injury (TBI) across the entire severity spectrum including diagnosis of mild TBI or/and determining mild TBI patients at risk of complications, and/or detection or monitoring status of spinal cord injury (SCI) in a subject. In one embodiment, the method comprises contacting a specimen of bodily fluid obtained from the subject with reagents for assaying for a marker of TBI selected from aldolase C (ALDOC) and brain lipid binding protein (BLBP/FABP7), or a trauma-specific break down product (BDP) of ALDOC or BLBP/FABP7. The method further comprises measuring the amount of marker present in the specimen as compared to a control sample, and determining the presence of TBI or SCI when an elevated amount of marker is present in the specimen compared to the control sample. In one embodiment, the marker of TBI is ALDOC and/or a BDP thereof, and BLBP and/or a BDP thereof. Optionally, the method further comprises measuring the amount of glutamine synthetase (GS), astrocytic phosphoprotein PEA-15 (PEA15), αB-crystallin (CRYAB/HSP27), a trauma-specific proteolytic cleavage product of ALDOC, GS, PEA15, or CRYAB, or any combination of two or more thereof. In one embodiment, the method further comprises measuring the amount of glial fibrillary acid protein (GFAP), or of a 20-30 kDa BDP of GFAP.

Representative examples of the trauma-specific proteolytic cleavage product of ALDOC include a 38 kDa major fragment, or a 35 kDa fragment, a 30 kDa fragment, and a 25 kDa fragment. An example of the trauma-specific proteolytic cleavage product for BLBP/FABP7 is a 3 kDa breakdown product. Examples of trauma-specific proteolytic cleavage product of GS include a 37+35 kDa doublet, a 32 kDa fragment, a 23 kDa fragment, a 20 kDa fragment, and 18 kDa fragment. Examples of the trauma-specific proteolytic cleavage product of PEA15 include a 12+13 kDa doublet and a 8 kDa fragment. Examples of the trauma-specific proteolytic cleavage product of αB-crystallin is selected from the group consisting of a 18+19 kDa doublet, a 17 kDa fragment, a 15+14 kDa doublet and a 8 kDa fragment.

In one embodiment, the method further comprises measuring the amount of a blood specific protein in a cerebrospinal fluid (CSF) sample obtained from the subject. The detection and monitoring of such markers can be used to determine the status of intraventricular brain bleeding post-injury. In one embodiment, the blood specific protein is apolipoprotein B (APOB). In another embodiment, the method further comprises measuring the amount of prostaglandin synthase (PTGDS) in a cerebrospinal fluid (CSF) sample obtained from the subject. PTGDS, also known as beta trace protein, is abundant in control, non-TBI CSF positively correlated with a healthy CSF composition. The presence of TBI is determined when the amount of PTGDS is reduced, and rises with recovery. The detection and monitoring of such markers as an elevated blood-specific protein or a reduced CSF protein after TBI can therefore be used to determine the status of recovery to control, or normal, levels after injury.

In some embodiments of the method, no additional markers are assayed beyond those recited herein. In other embodiments, only markers recited herein are assayed. In some embodiments, additional markers known to those skilled in the art are assayed in combination with markers recited herein. In other embodiments, only a subset of possible markers is assayed. For example, the method can comprise assaying for 2, 3, 4, 5, 6, 7, 8, 9, 10, 12, 15, or 20 markers. In one particular embodiment, no more than 4 markers are assayed.

The reagents for use in the method of the invention can comprise antibodies or other molecules that specifically bind the marker of TBI. In one embodiment, the measuring comprises immunoassay. Examples of immunoassays include western blotting, immunofluorescence, immunoluminescence, radioimmunoassay, and enzyme linked immuno-sorbent assay (ELISA).

In another embodiment, the reagents comprise protein-sequence and -fragment-specific peptides. Such reagents are useful for methods in which the measuring comprises targeted quantitative mass spectrometry. In one embodiment, the measuring comprises quantitative signal detection of endogenous (in the sample) proteo-typic peptides that are compared to added ('spiked in') labeled (e.g., heavy isotope labeled) known amounts of the same proteo-specific peptides (internal standards) using multiple or parallel reaction monitoring mass spectrometry.

In one embodiment, the control sample is a pre-injury sample obtained from the subject. In another embodiment, the control sample is representative of normal, healthy subjects, such as an average value obtained from a control cohort of healthy subjects.

Representative examples of a specimen of bodily fluid for use in the invention include, but are not limited to, plasma, serum, cerebrospinal fluid (CSF), nasal fluid, cerumen, urine, saliva, lacrimal tears, and brain microdialysate.

The invention additionally provides a kit comprising agents that specifically bind a set of biomarkers. In one embodiment, the biomarkers comprise aldolase C (ALDOC) and brain lipid binding protein (BLBP). The agents are typically polynucleotides or antibodies, and optionally labeled with a detectable marker. The kit optionally further consists of at least one container for housing the agents and/or instructions for use of the agents for determining status of traumatic brain injury in a test sample. In some embodiments, the kit comprises agents that specifically bind astrocytic phosphoprotein PEA-15 (PEA15) and/or a 20-30 kDalton fragment of glial fibrillary acid protein (GFAP-BDP), either alone or together with additional markers described herein or known in the art. In one embodiment, the antibodies are monoclonal antibodies. In one embodiment, the set of biomarkers consists of up to 3, 4, 5, 6, 7, 8, 9, or 10 biomarkers.

The invention further provides a method of determining the expression of the biomarkers ALDOC and BLBP in a sample of serum obtained from a subject. In one embodiment, the method comprises contacting the serum sample with a kit of the invention and measuring the binding of the agents to the biomarkers.

Also provided is a method of determining the status of traumatic brain injury in a sample of serum obtained from a subject. In one embodiment, the method comprises contacting the serum sample with a kit of the invention and measuring the binding of the agents to the biomarkers, and comparing the binding to a control sample. TBI is then determined to be present if the binding of the agents to ALDOC and BLBP is increased in the serum sample from the subject relative to the control sample. The invention further provides a method of detecting TBI in a subject. In one embodiment, the method comprises assaying a specimen of bodily fluid from the subject for an elevated amount of ALDOC and BLBP compared to a control sample. An elevated amount of ALDOC and/or BLBP is indicative of TBI. In one embodiment, the assaying is performed within 24 hours of a suspected injury, and up to one week post-injury. In some embodiments, the assaying is performed within 1-3 hours, or as early as within 15-30 minutes, of a suspected injury. In some embodiments, the subject is an infant or child, including, for example, a subject suspected of having experienced shaken baby syndrome. Suitable for this use is a biomarker expressed in the early developing brain, such as ALDOC or BLBP. In another embodiment, the subject is elderly, and the method is used to distinguish between TBI and chronic neurodegenerative disease, by measuring a ratio of ALDOC to its breakdown product.

The invention additionally provides a method of predicting outcome of TBI and/or recovery of ambulation after SCI in a subject. In one embodiment, the method comprises assaying a specimen of bodily fluid from the subject for an elevated amount of PEA15 or small BDPs of GFAP compared to a control sample or to a sample of a TBI survivor. wherein an elevated amount of PEA15 or small BDPs of GFAP is predicative of mortality. Also provided is a method of treating TBI in a subject. In one embodiment, the method comprises assaying a sample, obtained from the subject at multiple time points after injury (a longitudinal sample series) for a marker of TBI as described herein; and treating the patient for TBI if the assay indicates presence of TBI. This method can be used to monitor the status of the patient over time, and determine drug treatment efficacy, or whether an interventional treatment of the TBI patient would be indicated. Those skilled in the art will appreciate that each of the methods described herein can be performed with any one of the markers due to their very early postinjury release and prolonged detection window as well as variable biofluid clearance kinetic: ALDOC, BLBP, GS, PEA-15, CRYAB, a BDP of any of the foregoing; alone or in combination with one or more additional markers.

The markers ALDOC and BLBP, as well as PEA15 and CRYAB, are released from wounded, that is transiently compromised human brain cells and can therefore be used to track a concussion-relevant pathophysiological process, which is the brain's vulnerable state after injury. This association of these markers to a potentially reversible injury state provides patho-mechanistic information that can aid in making the diagnosis of mild TBI more sensitive, and can be valuable for pharmacokinetic monitoring of TBI patients beyond and in addition to tracking cell death released markers that reflect tissue loss.

BRIEF DESCRIPTION OF THE DRAWINGS

FIG. 4: Biplots showing that neurotrauma biomarkers are associated with cell fates of human traumatized astrocytes.

FIG. 11: Acute astroglial marker release correlated with histopathological severity measures, tissue loss and hemorrhage, after swine spinal cord injury.

FIG. 21: Immunoblot data showing that full size ALDOC is present in greater amounts than the 38 kDa BDP in acute TBI, whereas the two sizes of ALDOC are present in different ratios (given in Table 2) in the chronic neurodegenerative condition of Alzheimer's disease.

FIG. 22: Partitioning illustration of Table 3 thresholds.

DETAILED DESCRIPTION OF THE INVENTION

Figure 1:
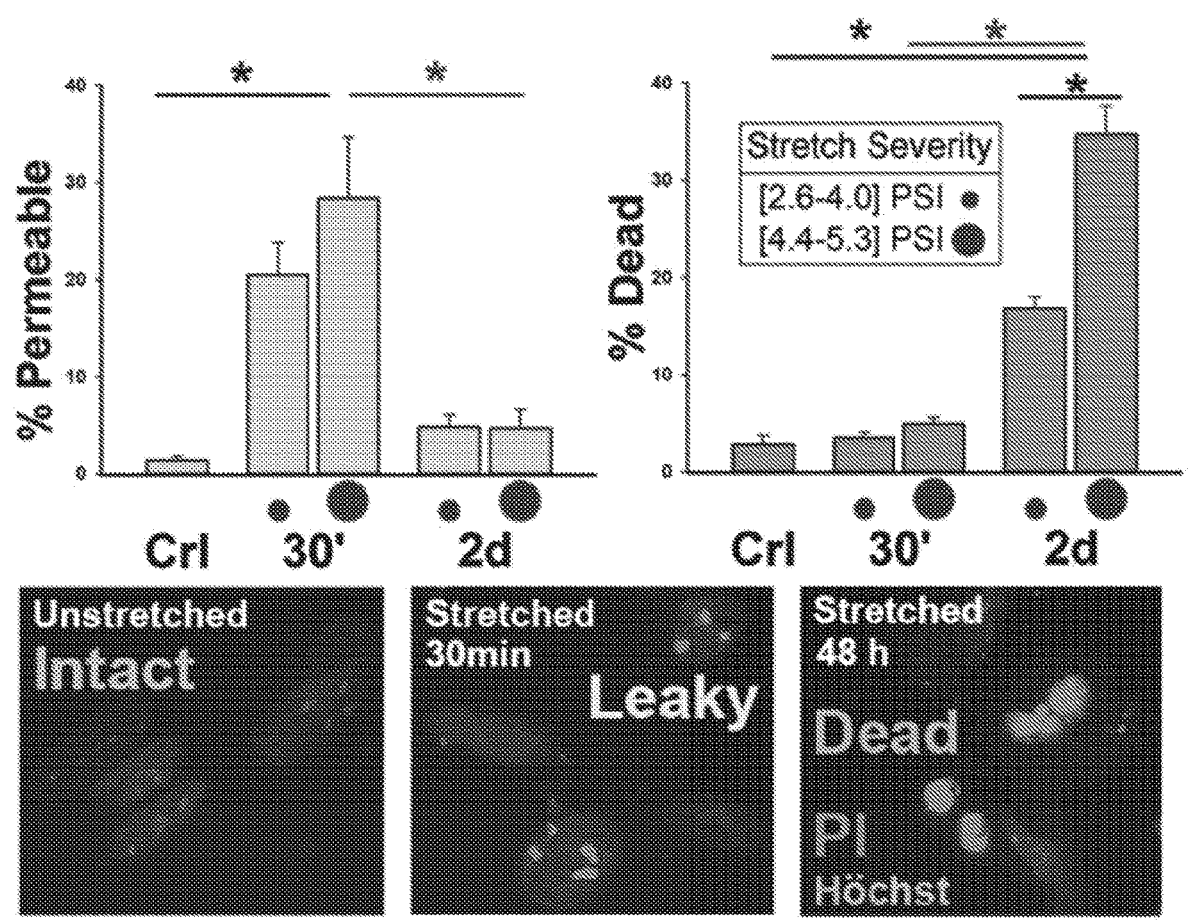
FIG. 1: Human neocortical astrocyte cell fates after mechanical trauma illustrated with bar graphs and photomicrographs of live-stained cells depicting nuclei of viable, leaky and dead cells.

The invention provides several new TBI biomarkers that were initially tested on CSF, plasma and serum from TBI patients and controls. New neurotrauma markers are defined by their release mechanisms to associate with cell wounding and/or cell death of human brain astroglia in a trauma model. Data presented herein demonstrate that select biomarkers show highly interesting kinetics and stability in body fluids. Immunological detectability, sensitivity and specificity is shown and suitable monoclonal antibodies have been selected. The timing of appearance of markers in CSF and serum during the first hours and days after TBI are presented in the accompanying Examples and Appendix. The results show that markers described herein and detectable in patient serum or plasma can be used to identify moderate and severe TBI, as well as mild TBI, and patterns indicative of fatal TBI. The markers are summarized in Table 1.

Definitions

All scientific and technical terms used in this application have meanings commonly used in the art unless otherwise specified. As used in this application, the following words or phrases have the meanings specified.

As used herein, "major", as in "major BDP", refers to the most frequently and consistently observed breakdown product, for example the 38 kDa BDP of ALDOC is the major BDP of ALDOC.

As used herein, "acute" refers to an early time post-injury time, typical the biofluid sample was collected on injury day for it to be considered acute. For example, 15-30 min after injury in trauma models, 1-2 hours post-injury in mild TBI patients, 3 hours to 24 hours post-injury in moderate and severe TBI patients.

As used herein, complicated mild TBI is used for concussion patients with positive computed tomography, CT/CAT scan finding, or more broadly with lasting symptomology, based on Buki et al., 2015.

As used herein, a "significant difference" means a difference that can be detected in a manner that is considered reliable by one skilled in the art, such as a statistically significant difference, or a difference that is of sufficient magnitude that, under the circumstances, can be detected with a reasonable level of reliability. In the Examples provided, herein, log-transformed data followed Gaussian distribution, and were used for statistical analyses by an independent statistician. One can use repeated measures analysis of variance with non-constant variance, mixed model (Crowder and Hand, 1990). As data are linear when log-transformed, significant changes are typically manifold, even by orders of magnitude. In one example, increase or decrease between TBI and controls that range between 80 fold to 13,000 fold are observed and found to be significant. In another example, changes across different post-injury days between 6 to 32 fold are considered significant. In yet another example, changes between survivors and non-survivors of TBI are between 4 fold and 1,400 fold are observed and found to be significant. In yet another example, an increase of two-fold relative to a reference or control sample is considered significant.

As used herein, "control" or "control sample" refers to a sample that is representative of either normal levels, or obtained from a subject known to be healthy.

As used herein, "a" or "an" means at least one, unless clearly indicated otherwise.

TABLE 1

| Astroglial injury markers | | | |
|---|---|---|---|
| Name | ID, molecular weight | Breakdown products (BDPs) with size | Release mechanism, marker class Biomarker properties |
| Top tier markers | | | |
| Glial fibrillary acidic protein | GFAP, 50 kDa | Lower GFAP BDPs 29, 25, (23) kDa 19 + 20 doublet, sequence defined by mass spectrometry of traumatized astrocytes, TBI patient CSF and serum | Cell death marker, strong correlation to human astroglial death, not cell wounding. Small fragments are calpain and caspases activity dependent. Delayed presence in TBI blood Fast clearance from biofluids (CSF, blood). Brain specific and abundant Associates with TBI and SCI outcome and predicts SCI severity. |
| Fructose-1,6-bisphosphate aldolase C | ALDOC, 40 kDa | ALDOC BDPs 38 + 37 kDa doublet 35 + 30 kDa 25 kDa | Cell leak marker, strong correlation to human astroglial cell wounding, moderate correlation to cell death. Fast release & presence in TBI blood Long-lived in biofluids (CSF, blood) Has higher levels than GFAP in CSF and blood on later post-injury days. Highly brain enriched and abundant. Strong predictive association with SCI severity and outcome; trend to relate with TBI outcome. ALDOC BDPs present in AD patients. More robust than GFAP in infants with TBI and mild TBI patients. |
| Brain lipid binding protein Fatty acid binding protein 7 | BLBP, 15 kDa FABP7 | BLBP BDP 3 kDa | Cell leak and cell death marker Moderate correlations to both in traumatized human astrocytes. Fast release & presence in TBI blood Short-lived in biofluids (CSF, blood) Brain enriched; Suitable for TBI progression monitoring; BLBP/GFAP ratio differentiates TBI severity. Moderate correlation with SCI severity. |
| Second tier markers | | | |
| Astrocytic phosphoprotein 15 | PEA15, 15 kDa | PEA15 BDPs 13 + 12 kDa doublet 8 kDa | Cell leak marker, strong correlation with human astrocyte cell wounding. Fast release & presence in TBI blood Short-lived in biofluids (CSF, blood) |

TABLE 1-continued

Astroglial injury markers

| Name | ID, molecular weight | Breakdown products (BDPs) with size | Release mechanism, marker class Biomarker properties |
|---|---|---|---|
| Glutamine synthetase | GS, 45 kDa | GS BDPs 37, 35, 32 kDa 23, 20, 18 kDa triplet | Suitable for TBI progression monitoring Trend to relate with TBI mortality More stable in biofluids as BLBP and PEA15, but less stable than ALDOC Predictive of SCI severity |
| α Crystallin, B chain = Heath shock protein 27 | CRYAB, 21 kDa HSP27 | CRYAB BDPs 19 + 18, 17 kDa triplet 15 + 14 kDa doublet 8 kDa | Cell leak marker, strong correlation with human astroglial cell wounding, moderate correlation with cell death. Short-lived in biofluids (CSF, blood) CRYAB differentiates trauma severity |
| Standards, indicators for CSF samples | | | |
| Apolipoprotein B | APOB, 120-130 kDa | N/A | Bleeding indicator Secreted into blood from intestine & liver; absent from healthy CSF Associates with bleeding in TBI CSF. |
| Prostaglandin (D2) Synthase = β trace protein | PTGDS, 22 kDa | N/A | Healthy CSF standard Most abundant CSF protein. Secreted enzyme; Associates post-TBI with survival |

Methods of the Invention

The invention provides a method for detection or monitoring status of traumatic brain injury (TBI), mild TBI, and/or spinal cord injury (SCI) in a subject. The method can be used to determine the presence, progression, prediction, and discrimination of severity of TBI or SCI in a subject. In one embodiment, the method comprises contacting a specimen of bodily fluid obtained from the subject with reagents for assaying for a marker of TBI selected from aldolase C (ALDOC) and brain lipid binding protein (BLBP/FABP7), or a trauma-specific break down product (BDP) of ALDOC or BLBP/FABP7. The method further comprises measuring the amount of marker present in the specimen as compared to a control sample, and determining the presence of TBI or SCI when an elevated amount of marker is present in the specimen compared to the control sample. In one embodiment, the marker of TBI is ALDOC and/or a BDP thereof, and BLBP and/or a BDP thereof. Optionally, the method further comprises measuring the amount of glutamine synthetase (GS), astrocytic phosphoprotein PEA-15 (PEA15), αB-crystallin (CRYAB/HSP27), a trauma-specific proteolytic cleavage product of ALDOC, GS, PEA15, or CRYAB, or any combination of two or more thereof. In one embodiment, the method further comprises measuring the amount of glial fibrillary acid protein (GFAP), or of a 20-30 kDa BDP of GFAP.

The monitoring of elevation of BLBP and/or PEA15 on subsequent days post-TBI informs on secondary adverse events post-injury. For example, the detection of elevated levels of ALDOC, BLBP, GS and PEA15 can be used to calculate Factor A, and levels of GFAP, S100beta and APOB can be used to calculate Factor B, based on marker loadings to each factor. Factor A and Factor B combined can be used to partition patients by severity. Factor A and B thresholds provide boundaries between TBI survivors, non-survivors and controls. A patient assessment within a clinical trial or study can be more robust by using a kit that provides multiple biomarker readings and performing factor analysis. This provides a simplified approach to track individual patients within a highly variable cohort, as opposed to requiring very large cohort sizes that may not be financially and otherwise feasible. Each clinical trial or study cohort biomarker panel data can be entered into a database, standardized and each patient is assessed based on tissue demise/bleeding versus tissue compromise/wounding Factors. Using Factors representative of these two classes makes the assessment more robust, as one zero reading will not prevent the entire factor analyses from providing a relative status output for any given patient. Boundaries pin out the severity spectrum of each cohort within which each patient will have a unique status at a given time post-injury In one embodiment, the method further comprises calculating a ratio between amounts of BLBP, an example of a cell leak marker, and GFAP, a cell death marker. The amounts can be measured using optical densities. Ratios between amounts of BLBP and GFAP in the trauma model range from 0.6-1.2 correspond to mild/moderate trauma, while ratios between 0.1-0.4 correspond to severe trauma. This reflects the finding in the human culture trauma model that, in severe trauma, there is proportionally more GFAP found than after mild trauma. BLBP/GFAP ratios in moderate TBI patients range between 0.4-0.3, whereas the range in severe TBI patients is between 0.01 and 0.05, again expressing a proportional larger GFAP to BLBP amount in severe versus moderate TBI patients. As such, using this ratio provides a more robust patient severity classification. By including two markers, significance is reached, whereas one marker alone would require a much larger cohort size. Use of marker combinations can thereby help in assessing TBI status and monitoring TBI progression, by reducing minimum required patient enrollment sizes when used as an evaluation tool in clinical studies or trials.

The method for detecting and monitoring status of TBI in a subject can be used to identify a subject at risk for complications after mild TBI or concussion. This identification is made by using acute presence, such as using samples obtained within 1-2 hours and up to 17 hours post-injury of BLBP and/or PEA15, in addition to ALDOC in serum samples. ALDOC elevation alone can identify a concussion, and injury day elevation of ALDOC and BLBP and/or PEA15 is associated with risk for complications.

Representative examples of the trauma-specific proteolytic cleavage product of ALDOC include a major 38 kDa fragment that was found most consistently, a 35 kDa fragment, a 30 kDa fragment, and a 23 kDa fragment. Examples of the trauma-specific proteolytic cleavage product of GS include a 37+35 kDa doublet, a 32 kDa fragment, a 23 kDa fragment, a 20 kDa fragment, and 18 kDa fragment. Examples of the trauma-specific proteolytic cleavage product of PEA15 include a 12+13 kDa doublet and a 8 kDa fragment. Examples of the trauma-specific proteolytic cleavage product of αB-crystallin is selected from the group consisting of a 18+19 kDa doublet, a 17 kDa fragment, a 15+14 kDa doublet and a 8 kDa fragment.

The ratio of amount of ALDOC full size (40 kDa) to amount of ALDOC cleavage product (38 kDa) is indicative for time post-injury, as well as distinction of acute versus subacute versus chronic brain injury or neurodegenerative brain disease, including Alzheimer's disease (AD). Thus, in one embodiment, the method of detecting and/or monitoring TBI or SCI comprises determining the ratio of 40 kDa ALDOC to 38 kDa ALDOC levels in the specimen obtained from the subject. A ratio larger than 1, ranging from 3.6-8.6, is indicative of TBI (acute and subacute, over post-injury days 1-5), as full size ALDOC is much more abundant than the 38 kDa ALDOC BDP. A ratio smaller than 1, ranging 0.4-0.6 is indicative of Alzheimer's disease, as the 38 kDa ALDOC BDP was similar or more abundant than the full size ALDOC optical signal density because a chronic degenerative condition allows for long-term partial degradation and accumulation of the fragment than an acute injury condition.

In one embodiment, the method further comprises measuring the amount of a blood specific protein in a cerebrospinal fluid (CSF) sample obtained from the subject. The detection and monitoring of such markers can be used to determine the status of intraventricular brain bleeding post-injury. In one embodiment, the blood specific protein is apolipoprotein B (APOB). In another embodiment, the method further comprises measuring the amount of prostaglandin synthase (PTGDS) in a cerebrospinal fluid (CSF) sample obtained from the subject. PTGDS, also known as beta trace protein, is positively correlated with a healthy CSF composition. The presence of TBI is determined when the amount of PTGDS is reduced, and rises with recovery. The detection and monitoring of such markers can therefore be used to determine the status of recovery to healthy levels after injury. In some embodiments, recovery of acute trauma-reduced PTGDS levels is monitored over subsequent post-injury days and is predictive of survival, while sustained reduced levels of PTGDS predict mortality.

In some embodiments of the method, no additional markers are assayed beyond those recited herein. In other embodiments, only markers recited herein are assayed. In some embodiments, additional markers known to those skilled in the art are assayed in combination with markers recited herein. In other embodiments, only a subset of possible markers is assayed. For example, the method can comprise assaying for 2, 3, 4, 5, 6, 7, 8, 9, 10, 12, 15, or 20 markers. In one particular embodiment, no more than 4 markers are assayed.

The reagents for use in the method of the invention can comprise antibodies or other molecules that specifically bind the marker of TBI. In one embodiment, the measuring comprises immunoassay. Examples of immunoassays include western blotting, immunofluorescence, immunoluminescence, radioimmunoassay, and ELISA. ALDOC isoform specific antibodies are available as monoclonal antibodies clones 4A9, 1A1, 5C9 and E9 from EnCor Biotechnology Inc. (Gainesville, Fla.). BLBP specific monoclonal antibodies are also available from EnCor Biotech Inc.

In another embodiment, the reagents comprise protein-sequence and -fragment-specific peptides. Such reagents are useful for methods in which the measuring comprises targeted quantitative mass spectrometry. In one embodiment, the measuring comprises quantitative signal detection of endogenous (in the sample) proteo-typic peptides that are compared to added ('spiked in') labeled (e.g., heavy isotope labeled) known amounts of the same proteo-specific peptides (internal standards) using multiple or parallel reaction monitoring mass spectrometry.

In one embodiment, the control sample is a pre-injury sample obtained from the subject. In another embodiment, the control sample is representative of normal, healthy subjects, such as an average value obtained from a control cohort of healthy subjects.

Representative examples of a specimen of bodily fluid for use in the invention include, but are not limited to, plasma, serum, cerebrospinal fluid (CSF), nasal fluid, cerumen, urine, saliva, lacrimal tears, and brain microdialysate.

The invention further provides a method of determining the presence of the biomarkers ALDOC and BLBP in a sample of serum or plasma obtained from a subject. In one embodiment, the method comprises contacting the serum or plasma sample with a kit of the invention and measuring the binding of the agents to the biomarkers.

Figure 13:
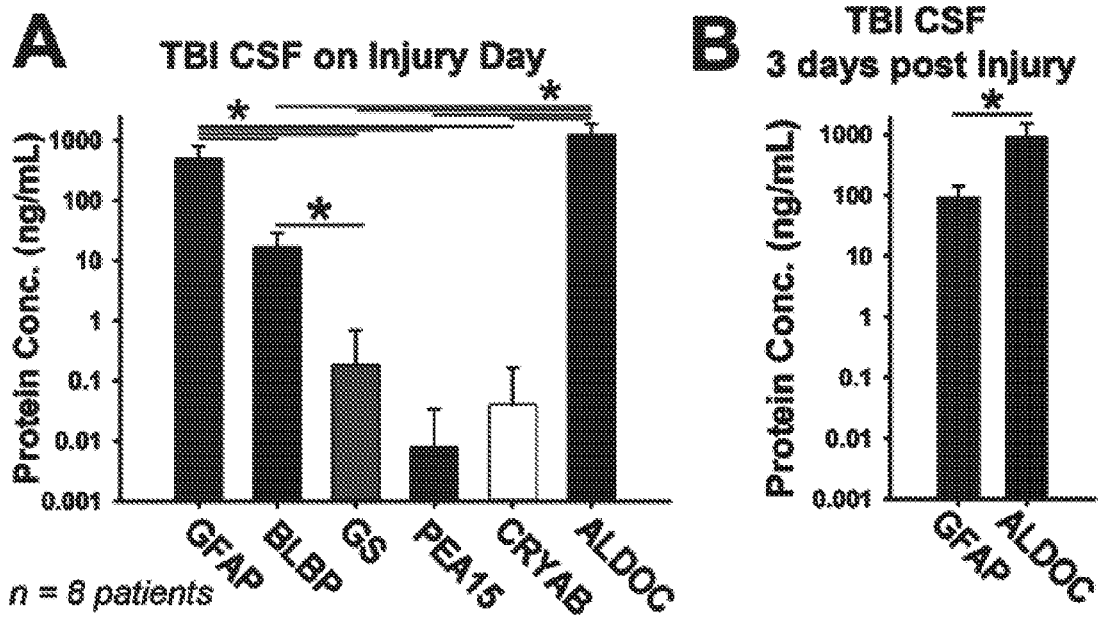
FIG. 13: Quantitative mass spectrometry, multiple reaction monitoring, documents concentration of astroglial TBI markers and allows marker amount comparison independent of antibodies.

Also provided is a method of determining the status of traumatic brain injury in a sample of serum or plasma obtained from a subject. In one embodiment, the method comprises contacting the serum/plasma sample with a kit of the invention and measuring the binding of the agents to the biomarkers, and comparing the binding to a control sample. TBI is then determined to be present if the binding of the agents to ALDOC and BLBP is increased in the serum sample from the subject relative to the control sample. For moderate to severe TBI patients, amounts and concentration ranges for ALDOC and BLBP are given in FIG. 14 and Example 13, and biomarker comparisons are given with concentrations in FIG. 13 and Example 12. The invention further provides a method of detecting TBI, in a subject. In particular, it can be used to detect mild TBI, where diagnosis is not otherwise obvious. In one embodiment, the method comprises assaying a specimen of bodily fluid from the subject for an elevated amount of ALDOC and BLBP compared to a control sample. An elevated amount of ALDOC and/or BLBP is indicative of TBI. In one embodiment, the assaying is performed within 24 hours of a suspected injury. In some embodiments, the assaying is performed within 1-3 hours, or as early as within 15-30 minutes, of a suspected injury. In one embodiment, the assaying is performed up to 7 days after a suspected injury. In some embodiments, the subject is an infant or child, including, for example, a subject suspected of having experienced shaken baby syndrome. The method allows for injury severity to be assessed, and outcome predicted in a subject, acutely after a spinal cord injury.

The invention additionally provides a method of predicting outcome of TBI and/or recovery after SCI in a subject. In one embodiment, the method comprises assaying a specimen of bodily fluid from the subject for an elevated amount of PEA15 and/or 20-30 kDa (small) GFAP fragments compared to a control sample, wherein an elevated amount of PEA15 and/or small (i.e. lower) GFAP fragments is predicative of mortality. Also provided is a method of treating TBI in a subject. In one embodiment, the method comprises assaying a sample obtained from the subject for a marker of TBI as described herein; and treating the patient for TBI if the assay indicates presence of TBI. The invention further provides a method of monitoring for treatment guidance in a subject being treated for TBI. In one embodiment, the method comprises assaying a sample obtained from the subject for a marker of TBI as described herein; and initiating a treatment of the patient for TBI if the assay indicates concerning deterioration of the patients status during the days post-injury, i.e. showing secondary elevated levels of any of the markers described herein. The methods of the invention additionally provide pharmacokinetic (theragnostic) applications, that is use in monitoring drug or other patient treatment for early evaluation of treatment effects and to monitor TBI progression post-injury. Those skilled in the art will appreciate that, given the different release and clearance kinetics of the markers described herein, the benefit of using multiple markers described herein as a panel. Thus the patients' assessment can include any one of the markers: ALDOC, BLBP, GS, PEA-15, CRYAB, a BDP of any of the foregoing; alone or in combination with one or more additional markers.

Some embodiments contemplated by the invention include use of a combination of TBI markers, including aldolase C (ALDOC), glutamine synthetase (GS), astrocytic phosphoprotein PEA-15 (PEA15), αB-crystallin (CRYAB), or brain lipid binding protein (BLBP/FABP7), a trauma-specific proteolytic cleavage product of ALDOC, GS, PEA15, CRYAB, or BLBP/FABP7, or any combination of two or more thereof. For example, embodiments include those in which the marker of TBI is GS and aldolase C, the marker of TBI is GS and PEA15, the marker of TBI is GS and αB-crystallin, the marker of TBI is GS and BLBP, the marker of TBI is aldolase C and PEA15, the marker of TBI is aldolase C and αB-crystallin, the marker of TBI is aldolase C and BLBP, the marker of TBI is PEA15 and αB-crystallin, the marker of TBI is PEA15 and BLBP, the marker of TBI is αB-crystallin and BLBP, the marker of TBI is GS, aldolase C, and PEA15, the marker of TBI is GS, BLBP, and PEA15, the marker of TBI is GS, αB-crystallin, and PEA15, the marker of TBI is GS, αB-crystallin, and BLBP, the marker of TBI is GS, αB-crystallin, and aldolase C, the marker of TBI is GS, BLBP, and aldolase C, the marker of TBI is aldolase C, PEA15, and αB-crystallin, the marker of TBI is aldolase C, PEA15, and BLBP, the marker of TBI is aldolase C, αB-crystallin, and BLBP, and the marker of TBI is PEA15, αB-crystallin, and BLBP. In the above examples, the TBI may be the recited protein, a breakdown product thereof, or both.

Kits

The invention additionally provides a kit comprising agents that specifically bind a set of biomarkers. In one embodiment, the biomarkers comprise aldolase C (ALDOC) and brain lipid binding protein (BLBP). The agents are typically polynucleotides or antibodies, and optionally labeled with a detectable marker. The kit optionally further consists of at least one container for housing the agents and/or instructions for use of the agents for determining status of traumatic brain injury in a test sample. In some embodiments, the kit further comprises agents that specifically bind astrocytic phosphoprotein PEA-15 (PEA15) and/or a 20-30 kDalton fragment of glial fibrillary acid protein (GFAP-BDP). In one embodiment, the antibodies are monoclonal antibodies. In one embodiment, the set of biomarkers consists of up to 3, 4, 5, 6, 7, 8, 9, or 10 biomarkers.

EXAMPLES

The following examples are presented to illustrate the present invention and to assist one of ordinary skill in making and using the same. The examples are not intended in any way to otherwise limit the scope of the invention.

Example 1: Human Neocortical Astrocyte Cell Fates after Mechanical Trauma

This Example shows population scores of human astrocytes 30 minutes and 48 hours after abrupt pressure-pulse traumatic stretching using different severities (FIG. 1; PSI ranges from 2.6-4.0 for milder injury and 4.4-5.3 for severe injury). Human astrocytes were isolated from 16-18 week donated fetal neocortical brain specimen, purified and then differentiated on deformable membranes (Wanner, 2012). Cell membrane wounding/compromise, mechanoporation (Barbee, 2005), was determined using Propidium iodide (PI) uptake in living cultures accompanied by nuclear shape assessment (middle picture, stained nuclei, Hoechst stained after fixation, with little pink dots, nucleoli that are PI-stained). Cell death was determined by PI uptake accompanied by condensed nuclei (pyknotic nuclei with compacted chromatin and bright Hoechst and PI stains). Significant percent of cell integrity compromise is shown 30 min post-injury (left graph) while significant cell death was present two days post-injury (bars on the right).

Figure 2:
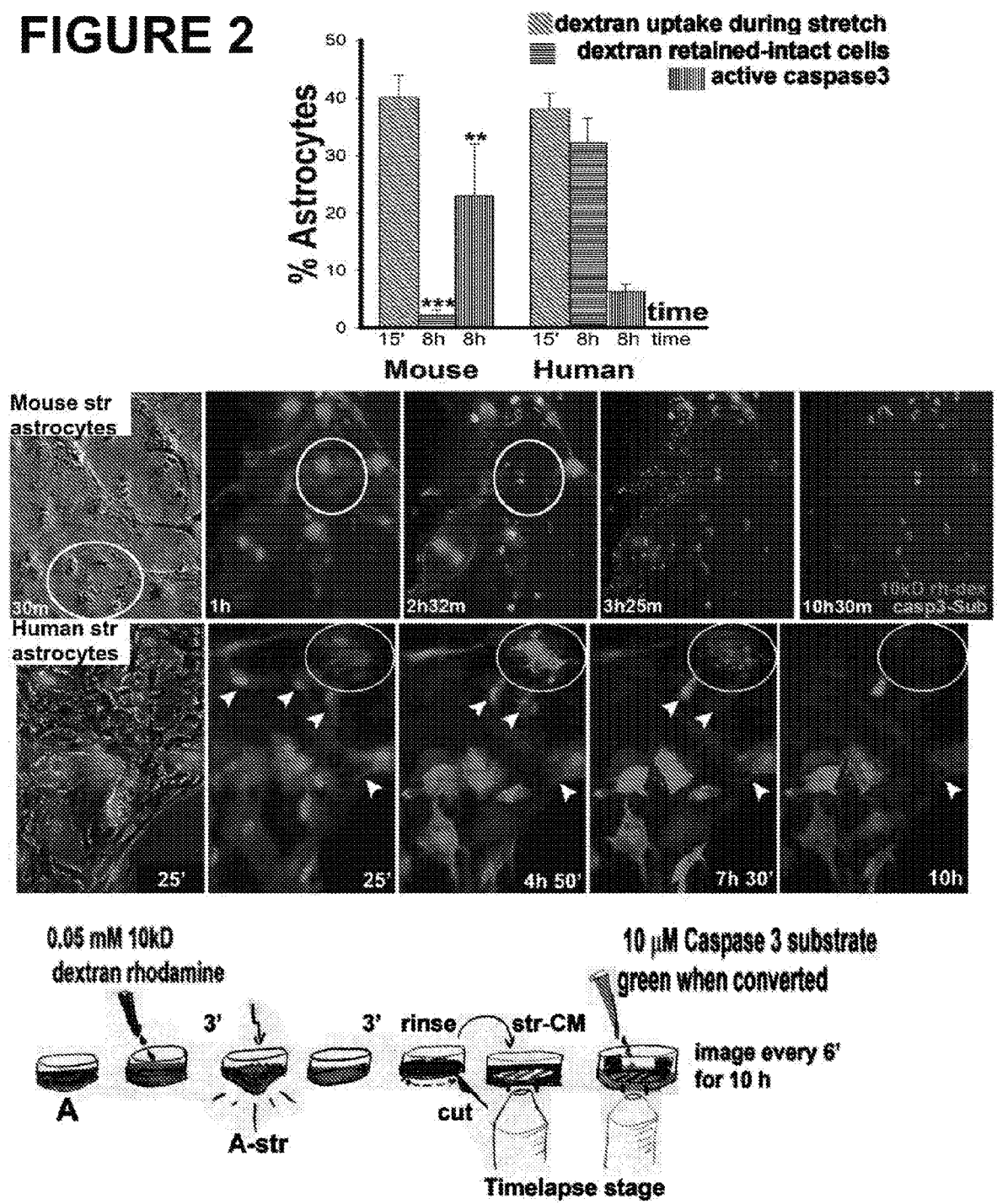
FIG. 2: Mechanically traumatized human astrocytes show prolonged endurance in a compromised state after wounding versus mouse astrocytes, as shown with a bar graph, a series of photomicrographs from time-lapse videos of live cells imaged on a temperature and gas controlled stage via confocal microscopy, and a schematic illustration of the protocol.

Example 2: Mechanically Traumatized Human Astrocytes Show Prolonged Endurance in a Compromised State This Example demonstrates that mechanically traumatized human astrocytes show prolonged endurance in a compromised state after wounding versus mouse astrocytes (FIG. 2). Dye uptake (0.05 mM 10 kDa dextran rhodamine) during stretch as well as cell death by apoptosis (caspase activation using 10 µM caspase 3 substrate) was monitored using time-lapse imaging on a temperature and humidity controlled spinning disc confocal microscope (Levine et al., 2016). Human traumatized wounded and resealed human astroglia show prolonged endurance after integrity compromise.

Figure 3:
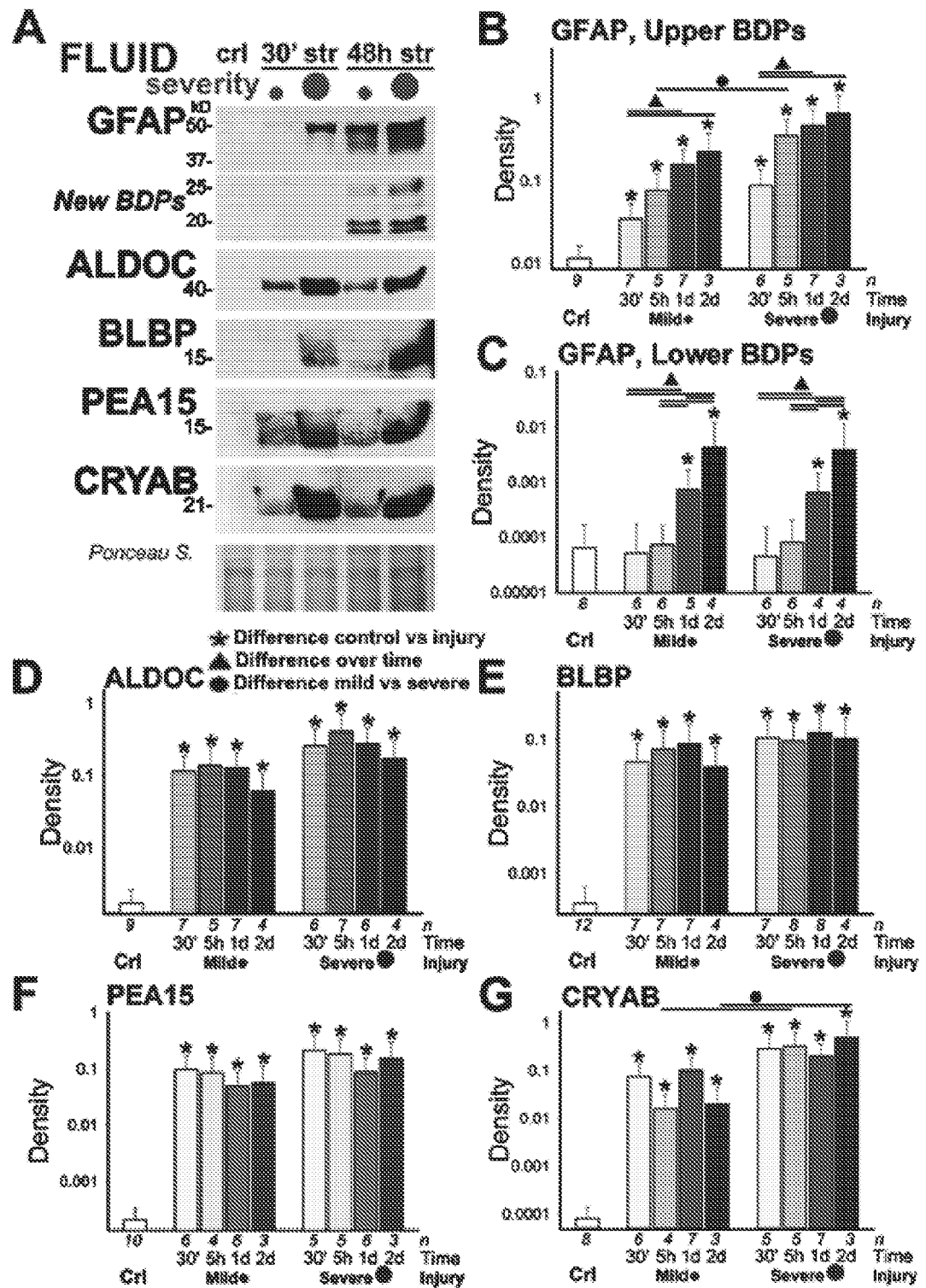
FIG. 3: Mechanical trauma of human astrocytes causes significant release of astroglial markers into surrounding fluids, as illustrated with immunoblots (A), and bar graphs showing amounts of marker at various time points after injury (B-G).

As shown in FIG. 3, mechanical trauma of human astrocytes causes significant release of astroglial marker into surrounding fluids. FIG. 3A shows immunoblots of concentrated, denatured conditioned media (Levine et al., 2016; Sondej et al., 2011) from traumatized astrocytes show different release profiles of glial fibrillary acidic proteins (GFAP) and its known and newly-identified breakdown products (BDPs) versus aldolase C (ALDOC), brain lipid binding protein (BLPB), astrocytic phosphoprotein (PEA15) and α crystallin (CRYAB). In order to capture the full range of signal intensity, signals from multiple exposures of immunoblots were densitometrically measured (optical densities) and scaled to match a single exposure. Scaled densities of signals from indicated number of donors are plotted on log-spaced axis in the graphs shown in FIG. 3B-G. Known upper GFAP BDPs (between 37-50 kDa) showed increased release with time (triangles) and seventy (circle at 5 hours post-injury). New, lower GFAP BDPs were significantly elevated only one and two days post-injury, associating them with cell death (see FIG. 1). ALDOC, BLBP and PEA15 were already significantly elevated 30 min post-injury over two orders of magnitude and such elevated levels remained in fluids at all post-injury times measured. CRYAB levels showed severity distinction at 5 hours and two days post-injury.

Example 3: Neurotrauma Biomarkers Associated with Cell Fates of Human Traumatized Astrocytes Shown in FIG. 4A are biplots of trauma-released astroglial marker levels (see FIG. 3) for ALDOC, BLBP, PEA15 and CRYAB over the percent membrane permeable cells (% wounded, red data, left) as well as correlated to percent of dead human traumatized astrocytes using PI-dye-update assay and nuclear morphology (see FIGS. 1+2). Regression lines (R2-value) and p-values indicate correlation significance. ALDOC, PEA15 and CRYAB show best correlation with human astroglial cell wounding. CRYAB, BLBP and ALDOC also correlated with extend of cell death after trauma.

FIG. 4B shows biplots of GFAP trauma-release, which show correlation of GFAP with cell death inflicted by mechanical trauma and weak/no correlation with cell wounding. Plots are separated by grouped GFAP fragment sizes (upper bands: 50-37 kD, lower bands: 25-19 kD).

Example 4: Astrocyte Injury Biomarker Selection Strategy

Figure 5:
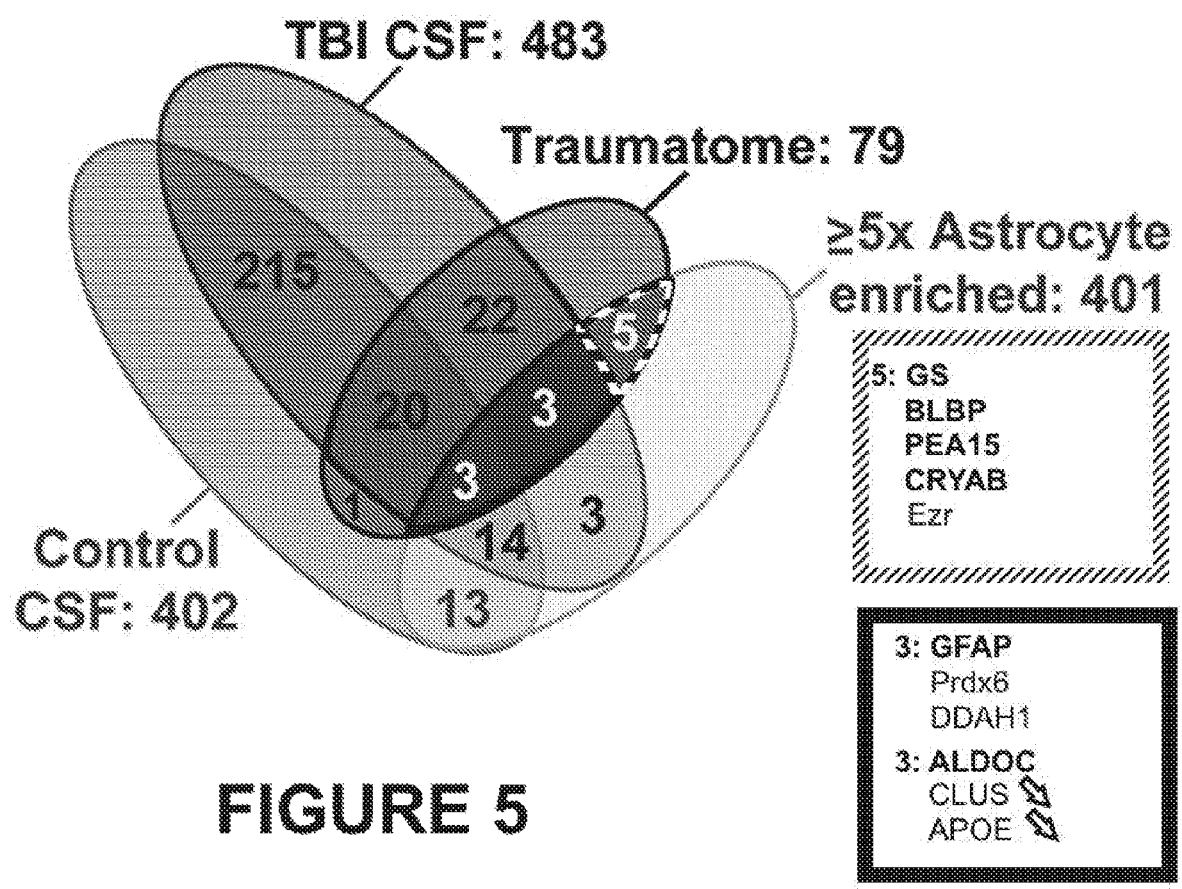
FIG. 5: Schematic illustration of astrocyte injury biomarker selection strategy.

Candidate astrocyte injury biomarkers were selected by the following strategy (FIG. 5). A TBI CSF proteome was compiled by bottom-up mass spectrometry using CSF samples from 19 severe TBI patients and compared with the CSF proteome from 9 control subjects (Crl). This TBI CSF proteome (483 proteins) overlapped with 252 proteins from the control CSF proteome (402 proteins), leaving 231 unique TBI CSF proteins. Sixty percent of the TBI CSF proteins were also present in the published plasma proteomes (Omenn et al., 2005; Schenk et al., 2008) and, if abundant, may not be suitable as TBI biomarkers. To select candidate brain injury markers, we determined proteins released from traumatized astrocytes using a proteomic approach in a simple trauma model 79 differentially released proteins were identified after pressure-pulse stretching mouse astrocytes (Levine et al., 2015; Sondej et al., 2011).

From this "traumatome" 48 proteins (62%), were present in TBI CSF. Selecting for highly astrocyte-enriched proteins (>/=5 fold enrichment over other cell types, Cahoy et al., 2008) yielded a small candidate pool of 11 injury biomarker proteins (black outlined enclosed 3 fields). These included 3 proteins GFAP and peroxiredoxin 6 (Prdx6, both present in plasma) and N,N-dimethyl arginine dimethyl aminohydrolase (DDAH1, center field of 3). Additional 3 proteins were astrocyte enriched, "traumatome" proteins present in TBI CSF and also in control CSF that were aldolase C (ALDOC), clusterin (CLUS) and apolipoprotein E (APOE, lower field of 3). Clusterin and APOE are secreted by astrocytes and their levels decreased in fluid after trauma (arrow). Additional 5 trauma-released proteins that were highly astrocyte enriched were not listed in the shotgun mass spectrometry-based TBI CSF proteome list. These 5 were ezrin (Ezr), F-box only protein 2 (FBX2), Glutamine synthetase (GS), astrocytic phosphoprotein 15 (PEA15) and brain-lipid binding protein (BLBP, upper field of 5, dashed outline). GFAP, ALDOC, GS, BLBP, PEA15 and CRYAB were included in subsequent immunological and mass spectrometry testing.

Figures 6A, 6B, 6C:
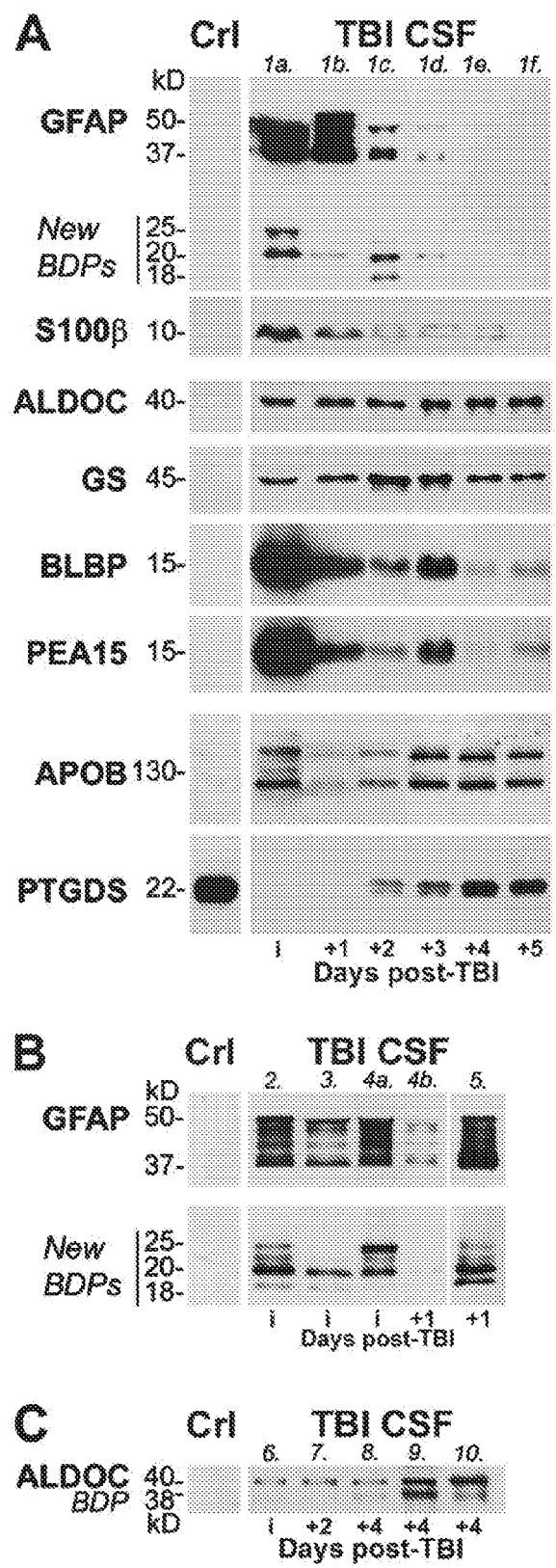
FIGS. 6A-6K: Immunoblots (6A-6C) and scatter-plots plotted jointly with box and whisker plots (6D-6K) with interquartile ranges (90th and 10th percentiles), median (line) and geometric mean (dashed line) showing logarithmic scaled optical densities measured from immunoblot signals using scaled densitometry (see FIG. 3) in CSF of 20-25 TBI patients on injury day and subsequent 5 post-injury days and 8-11 Controls (n: subjects numbers per day), showing that astroglial injury markers are elevated in CSF of TBI patients versus controls in a retrospective observational cohort on injury day and consecutive 5 days post-injury.

Example 5. Astroglial Injury Markers are Elevated in CSF of TBI Patients on Injury Day and 5 Consecutive Days Post-Injury This Example demonstrates that astroglial injury markers are elevated in CSF of TBI patients versus controls in a retrospective observational cohort on injury day and for five consecutive days post-injury. FIG. 6A shows immunoblots of GFAP (50 kDa with BDPs 37, 25, 20 and 18 kDa) and S100β and ALDOC (40 kDa), GS (45 kDa), BLBP (15 kDa) and PEA15 (15 kDa) of a longitudinal set of 30 µl CSF samples from injury day (i) and subsequent 5 days post-injury (i+1 to i+5) of a 54 year old male severe TBI patient (1a-1f.) alongside with 30 µl control CSF (Crl). BLBP and PEA15 showed strongest signals on injury day and second rise on 3rd post-injury day, that associated with this patient's secondary ischemic episode. Bleeding indicator APOB (130 and 250 kDa) had variable intensity over time post-injury and was absent from healthy CSF; CSF marker PTGDS (22 kDa) had robust signal in Crl CSF but was absent acutely after TBI and one day post-injury and stepwise recovered signals on subsequent post-injury days.

FIG. 6B shows six CSF samples (30 µl/lane) from four TBI patients (2.-5.), illustrating variable signal intensities of GFAP and "upper" BDPs between 50 and 37 kDa and "lower/new" GFAP BDPs including 25/23 kDa doublet, 20 kDa and 18 kDa small BDPs on injury day (patients 2, 3, 4a) and one day post-injury (4b, 5) alongside control CSF from a healthy 43 year old male. Individual bands within upper GFAP BDPs have similar intensities to each other, while relative abundance between lower GFAP BDPs was distinctly different across patients.

FIG. 6C shows CSF immunoblots (30 µl/lane), demonstrating full size ALDOC (40 kDa) in five TBI patients (6.-10.) and 38 kDa ALDOC BDP of variable intensity on four days post-injury in three TBI patients (8-10). A healthy Control subject showed no ALDOC.

Figure 6D:
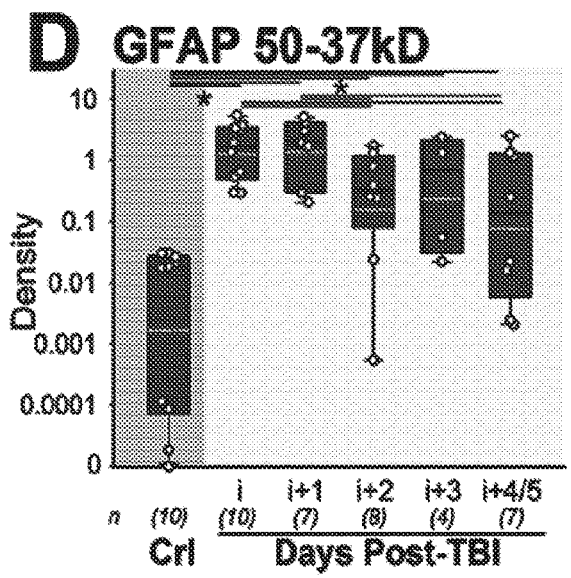
Figure 6E:
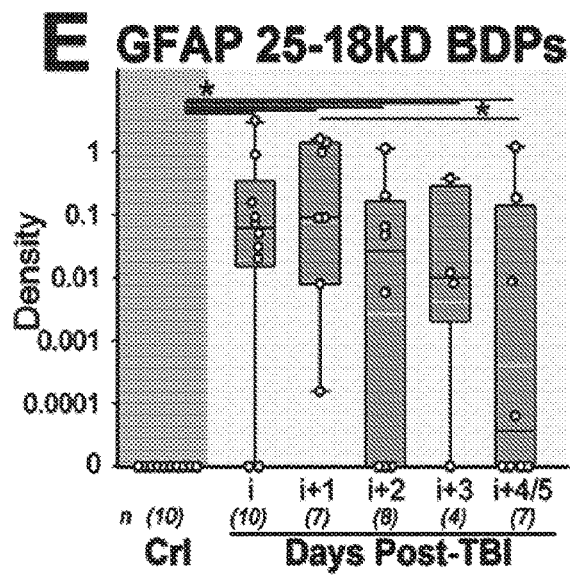
Figure 6F:
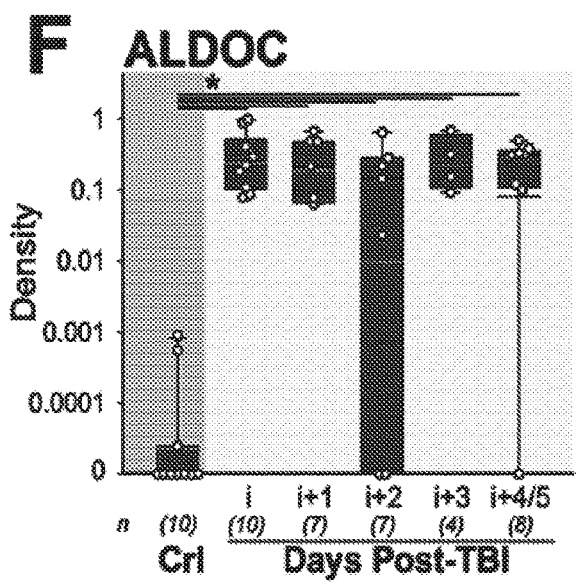
Figure 6G:
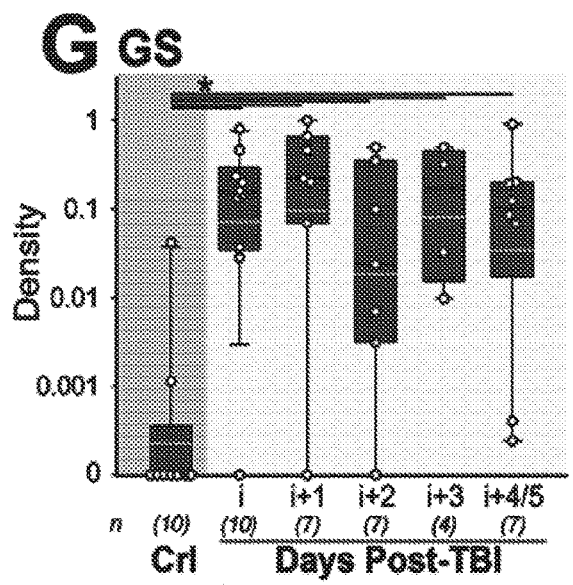
Figure 6H:
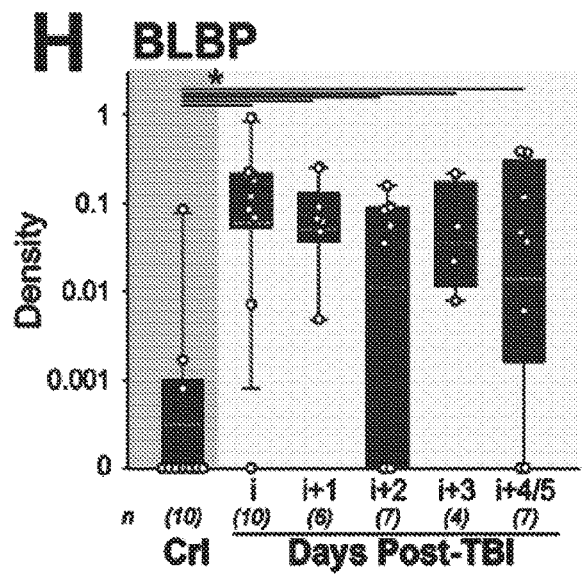
Figure 6I:
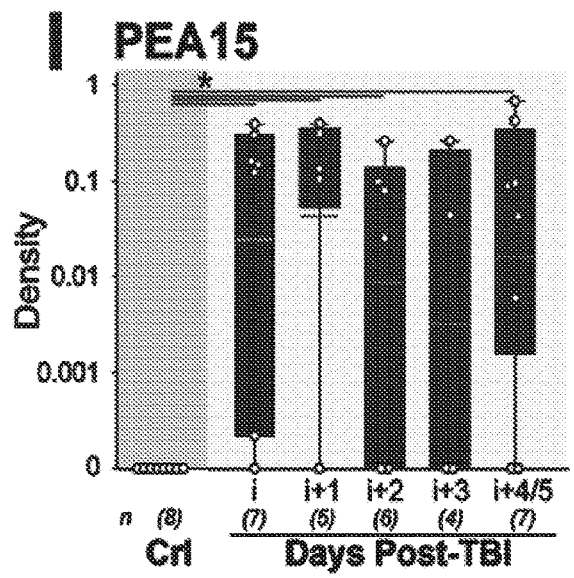
Figure 6J:
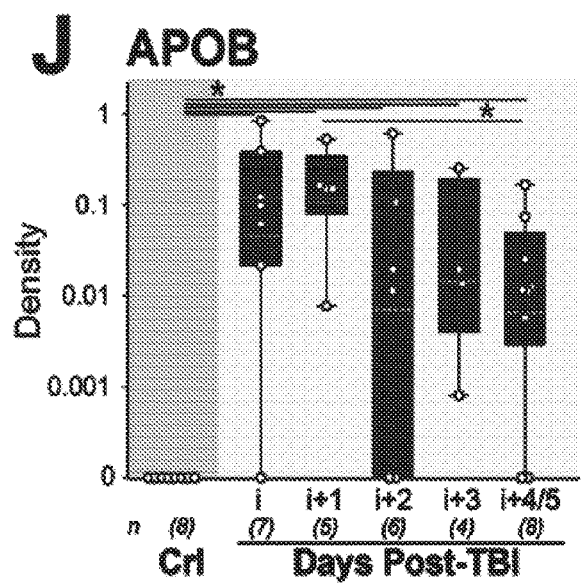
Figure 6K:
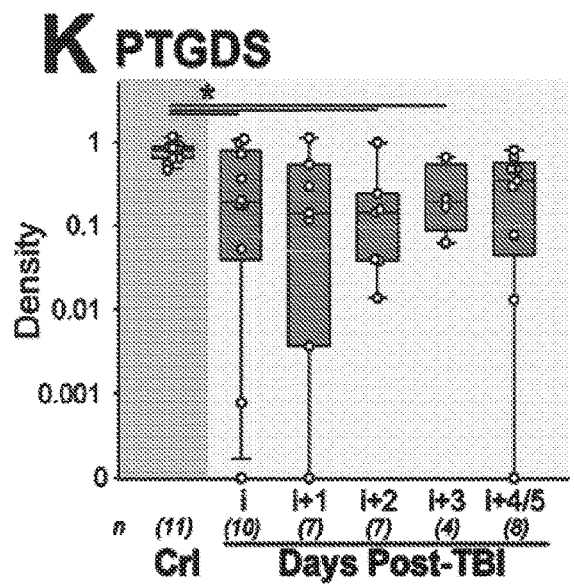

Scatter-plots (FIGS. 6D-K, same day and patient replicates averaged) are plotted jointly with box and whisker plots with interquartile ranges (90th and 10th percentiles), median (line) and geometric mean (dashed line) showing logarithmic scaled optical densities measured from immunoblot signals using scaled densitometry (see FIG. 3) in CSF of 20-25 TBI patients on injury day and subsequent 5 post-injury days and 8-11 Controls (n: subjects numbers per day). (FIG. 6D) Upper GFAP signals (50-37 kDa) were elevated on all TBI days versus Crl ($P<0.06$) and declined over time as indicated ($P<0.05$, repeated measures ANOVA, see Methods). (FIG. 6E) Lower GFAP BDPs (25-18 kD) were elevated in TBI versus Crl ($P<0.03$) and declined between first post-injury day later post-injury days ($P<0.05$). (FIG. 6F) ALDOC ($P<0.004$) and (FIG. 6G) GS ($P<0.001$) were elevated on each day in TBI CSF versus Crls without decline. (FIG. 6H) BLBP ($P<0.03$) and (FIG. 6I) PEA15 ($P<0.004$) had elevated levels in TBI versus Crls on indicated days with larger signal ranges. Serum protein APOB (FIG. 6J) was elevated in TBI versus Crl CSF ($P<0.005$), whereas CSF standard PTGDS was stronger in Crl versus TBI ($P<0.004$) with levels acutely depleted to various extents followed by outcome dependent recovery (see FIG. 7).

Example 6: TBI Patient Outcome Correlation of Biomarker CSF Amounts

Figure 7:
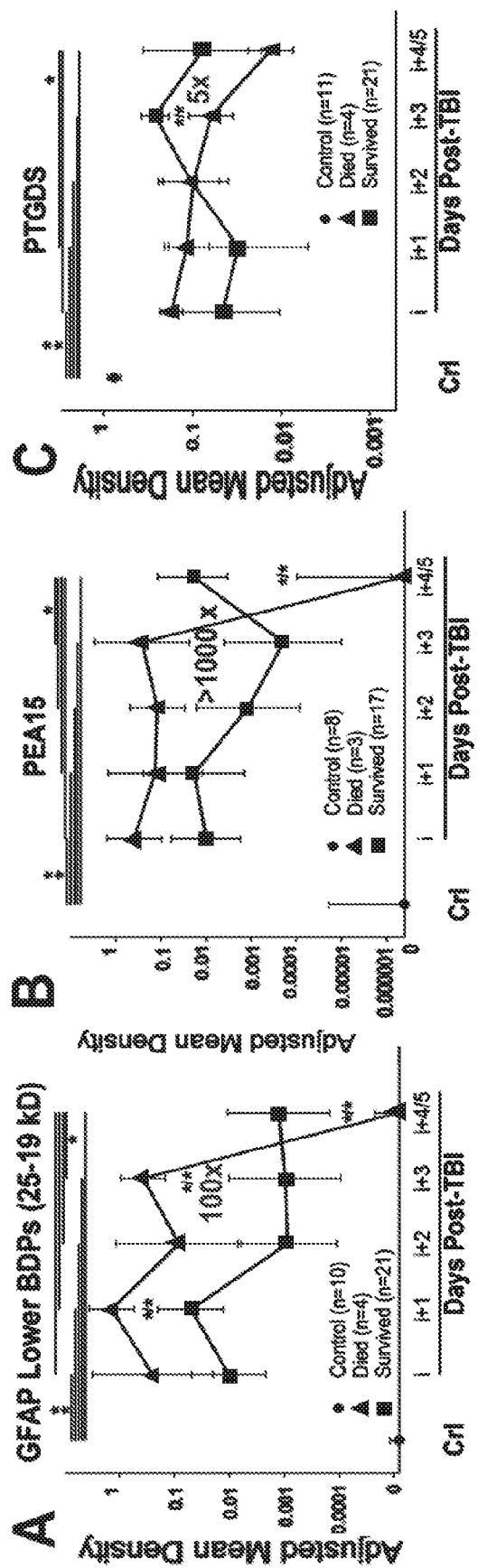
FIG. 7: TBI patient outcome correlation of biomarker CSF amounts.

This Example demonstrates that CSF levels of new, cell death associated lower GFAP breakdown products were two orders of magnitude more elevated in non-survivors versus survivors of TBI (FIG. 7). PEA15 levels were over 2-3 orders of magnitude elevated in non-survivors versus survivors after TBI, with p-value on the third post-injury day $p=0.07$. Levels of health marker PTGDS, which decreased acutely post-injury, showed significant recovery by the third post-injury day in survivors of TBI while levels remained decreased in non-survivors.

Figure 8:
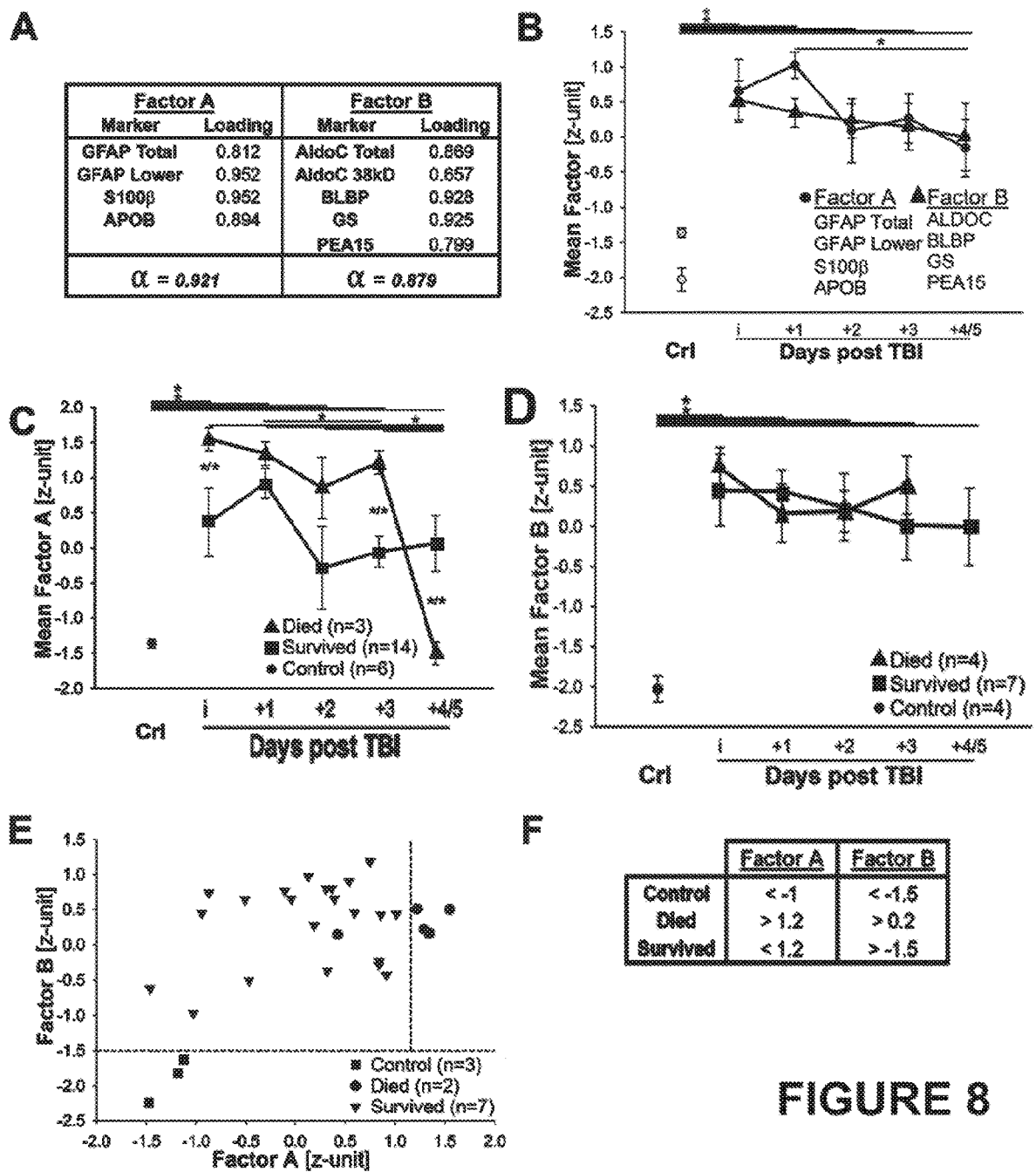
FIG. 8: Assessing the spectrum of TBI using factors of grouped astroglial injury markers.

Example 7: Assessing the Spectrum of TBI Using Factors of Grouped Astroglial Markers This Example demonstrates the grouping of astroglial trauma markers to create factors useful in the assessment of TBI across the spectrum of injury. To combine the diverse data encompassed by the marker panel, multivariate analysis of variance that employed an unsupervised learning algorithm based on Spearman correlation coefficients was used (factor analysis, Fabrigar and Wegener, 2012; Tucker, 1997). This approach is new to the neurotrauma biomarker field, and reveals underlying neurotrauma conditions by grouping markers here based on their TBI CSF signals. Known astroglial marker S100β, cell death markers GFAP with known and new BDPs, and bleeding indicator APOB were grouped into Factor A (FIG. 8A, gray, with combined loading using Cronbach's coefficient α=0.921). New 'cell leak', cell wounding markers ALDOC with BDP, BLBP, GS and PEA15, were grouped into Factor B (α=0.879). As shown in FIG. 8B, Factor A's temporal profile significantly decreased over days post-injury, while Factor B's trajectory did not. Factor A data showed significant difference between survivor and non-survivors on several post-injury days (FIG. 8C). Factor B data did not show survival differences (FIG. 8D). Standardized marker density readings from 12 TBI patients with signal present for all markers were converted into the Factors A and B using the loadings shown in FIG. 8A, and then plotted against each other (FIG. 8E). Heterogeneity among the TBI spectrum is reflected in the spread of the combined panel data in this biplot. Classification tree analysis (FIG. 8F) determined boundaries that partitioned controls, survivors and non-survivors of TBI according to given Factor thresholds (Breiman, 1984). Patient partitioning thresholds using the biomarker levels grouped into factors are illustrated by lines in FIG. 8E.

This mathematical multivariate unsupervised learning approach combines the markers of this panel with each marker given a weight (loading) that is derived from correlation coefficients and expresses how much variance in the patient cohort is captured by this marker's contribution. Overall high loading of the listed markers (0.8-0.95) documents robust categorization into the two factors. Factor A reflects markers associated with cell death, hemorrhage and tissue loss. Factor B reflects markers associated with cell leak, wounding and tissue compromise (see FIG. 8A). The resulting values document a unique position of each patient based on its biomarker panel readings within a given cohort. This approach reliably covers the majority of patient variation observed in this TBI cohort. Factor analysis provides a simplified framework for capturing a large patient heterogeneity observed in TBI using only few biomarker readings, (compared to more complex principal component analysis that used many different entries). In a clinical trial, these biomarker panel readings from a test kit can be entered into a growing database that can provide valuable monitoring information of individual TBI patients compared to other patients. This tool can simplify patient assessment and strengthen the robustness of ongoing patient evaluation using biofluid signature of tissue compromise and tissue demise.

Figure 9:
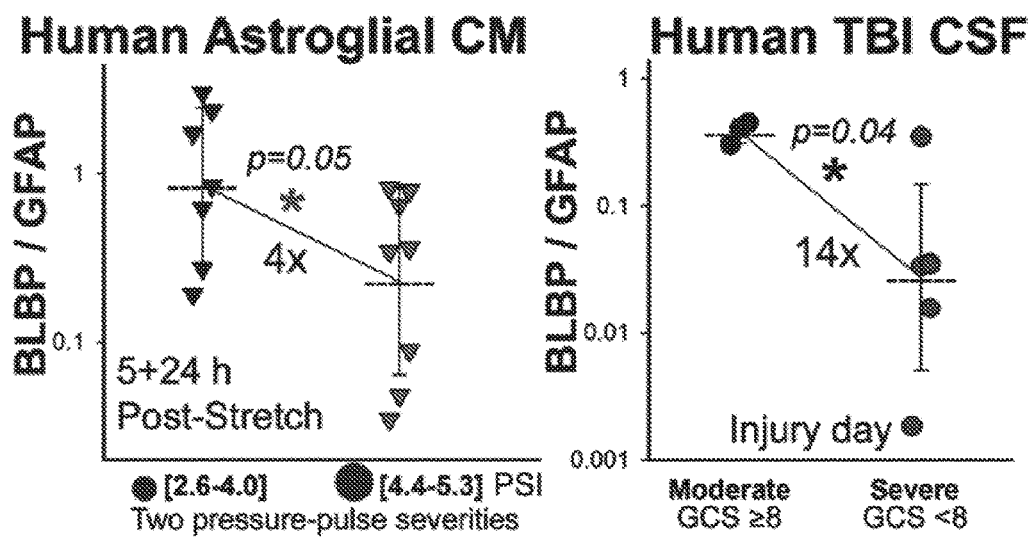
FIG. 9: Cell wounding over cell death—ratio of BLBP over GFAP differentiates trauma severity in human traumatized astrocytes and TBI patients.

Example 8: Differentiating Trauma Severity in Human Traumatized Astrocytes and TBI Patients This Example demonstrates that the ratio of BLBP to GFAP levels in a subject's specimen can be used to differentiate trauma severity in human traumatized astrocytes and TBI patients. Significant differences in fluid level ratios of 'cell leak' marker BLBP over 'cell death' marker GFAP are shown in vitro (FIG. 9, CM, conditioned medium, left) and in TBI patients (CSF, right panel of FIG. 9). Human astrocytes from 6 donors were traumatized with different severities using indicated PSI pressure-pulses. Moderate versus severe TBI patients are distinguished by 14 fold different BLBP/GFAP ratio in CSF (n=9). Moderate TBI patients are defined by post-resuscitation Glasgow coma scale (GCS)>8 while severe TBI patients had GCS<8.

Example 9: Correlation Between ALDOC Levels and TBI Patient Outcome

Figure 10:
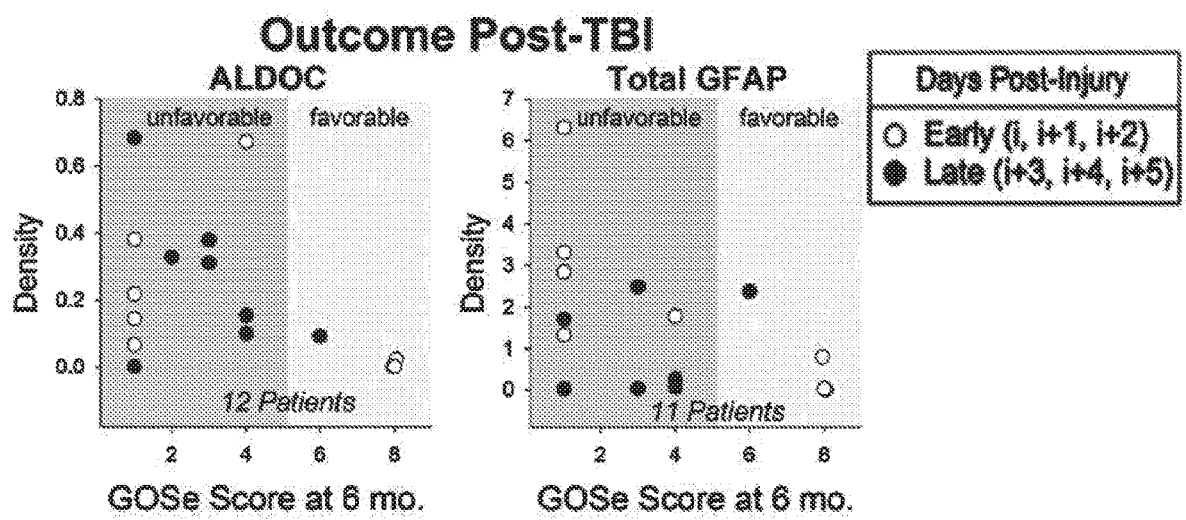
FIG. 10: Correlation between ALDOC levels and TBI patient outcome.

Data presented in FIG. 10 show ALDOC and GFAP levels plotted against outcome of severe TBI patients, assessed using extended Glasgow outcome score (GOSe) at 6 months post-TBI. Data from 12 (11) TBI patients show ALDOC elevation early (white, i, i+1, +2) and later post-injury (black, i+3, +4 and +5 post-injury days) in patients with unfavorable outcome, while GFAP levels did not as well maintain elevated levels on later post-injury days.

Example 10: Correlation Between TBI Markers and Severity and Outcome of Spinal Cord Injury This Example demonstrates the correlation between astroglial trauma markers and severity of spinal cord injury in a swine animal model. FIG. 11: Acute UCLA astroglial marker release correlated with histopathological severity measures, tissue loss and hemorrhage, after swine spinal cord injury. A) Acute (15-30 min post-injury) CSF signal densities of UCLA astroglial injury markers ALDOC, BLBP and glutamine synthetase (GS) as well as GFAP are plotted against rostro-caudal cavity diameters in the Yucatan swine spinal cord one week after spinal cord contusion injury using an established injury weight drop model (Lee et al., 2013). Spearman correlations indicate acute elevation of these astroglial CSF marker levels associated significantly with increasing tissue loss. Histopathology. Rostro-caudal extension of the cavity was measures in Sudan black stained horizontal spinal cord sections (p-values and $R^2$ values given, n=10 animals). B) Acute (15-30 min post-injury) CSF signal densities of ALDOC and GS significantly associated with white matter interstitial tissue bleeding one week post-injury that was measured using swine immunoglobulin (IgG) fluorescence in injured horizontal spinal cord sections and normalized by parallel stained uninjured horizontal spinal cord sections. Such normalized white matter fluorescence signals of rostro-caudal serial images were plotted for each animal (n=8 animals) and areas under the curves (AUC) were determined over distances with above uninjured signal levels.

Figure 12:
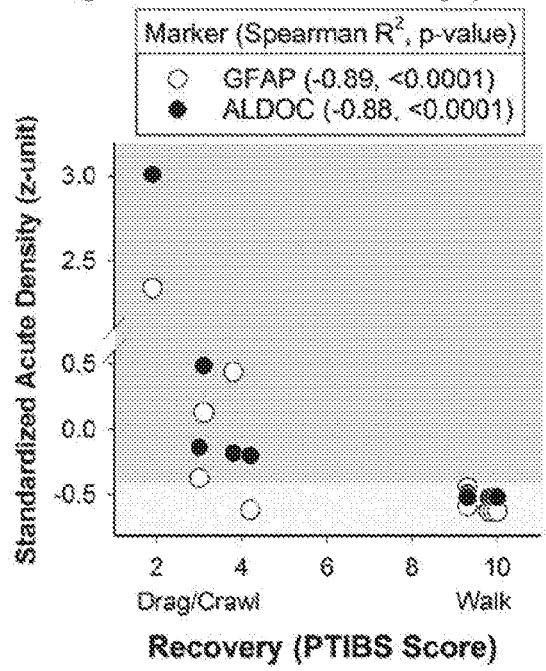
FIG. 12: Outcome correlation of acutely elevated ALDOC and GFAP after swine spinal cord injury.

FIG. 12 shows the correlation of acutely elevated ALDOC and GFAP with outcome after swine spinal cord injury. Recovery of walking associates with acute CSF levels of ALDOC and GFAP after swine spinal cord injury. Plotted are acute post-injury CSF levels (15-30 min post-injury) of ALDOC (black dots) and GFAP (white dots) that predicts recovery of walking one week post-injury using the porcine thoracic injury behavioral scale (PTIBS), an established test for recovery of ambulation in the swine indicating the level of walking recovery after spinal cord injury in the Yucatan swine (Lee et al., 2013). A significant inverse correlation existed with higher ALDOC ($R^2$ −0.88) and GFAP ($R^2$ −0.89) levels in poorly ambulating animals, who were dragging their hind limbs and crawled at best, and low acute ALDOC and GFAP levels in animals who walked by one week post-injury. Preliminary biomarker thresholds are indicated by background color, showing feasibility of very early partitioning of recovering animals.

Example 11: Quantitative Mass Spectrometry of Astroglial TBI Markers

This Example demonstrates that quantitative mass spectrometry confirms the increased levels of astroglial TBI markers following injury, providing objective marker amount comparisons that is limited when using immunological methods as these are not standardized. Multiple reaction monitoring, an antibody independent, simultaneous and quantitative mass spectrometry approach, was used for the first time in the neurotrauma biomarker field to compare abundance of known and new astroglial markers in CSF of TBI patients. Marker-specific peptides are measured in parallel with defined amounts of added, isotope-labeled peptides (see Table 6). FIG. 13A shows that ALDOC and GFAP had the highest concentrations in TBI CSF on injury day, and both differed significantly from levels of other markers shown. In addition, BLBP levels were significantly higher than GS levels on injury day. As shown in FIG. 13B, by 3 days post-TBI, ALDOC levels significantly out-performed GFAP concentrations, differing by an order of magnitude.

Example 12: Quantitative Immunoassay of ALDOC and BLBP in TBI CSF and Blood

Figure 14:
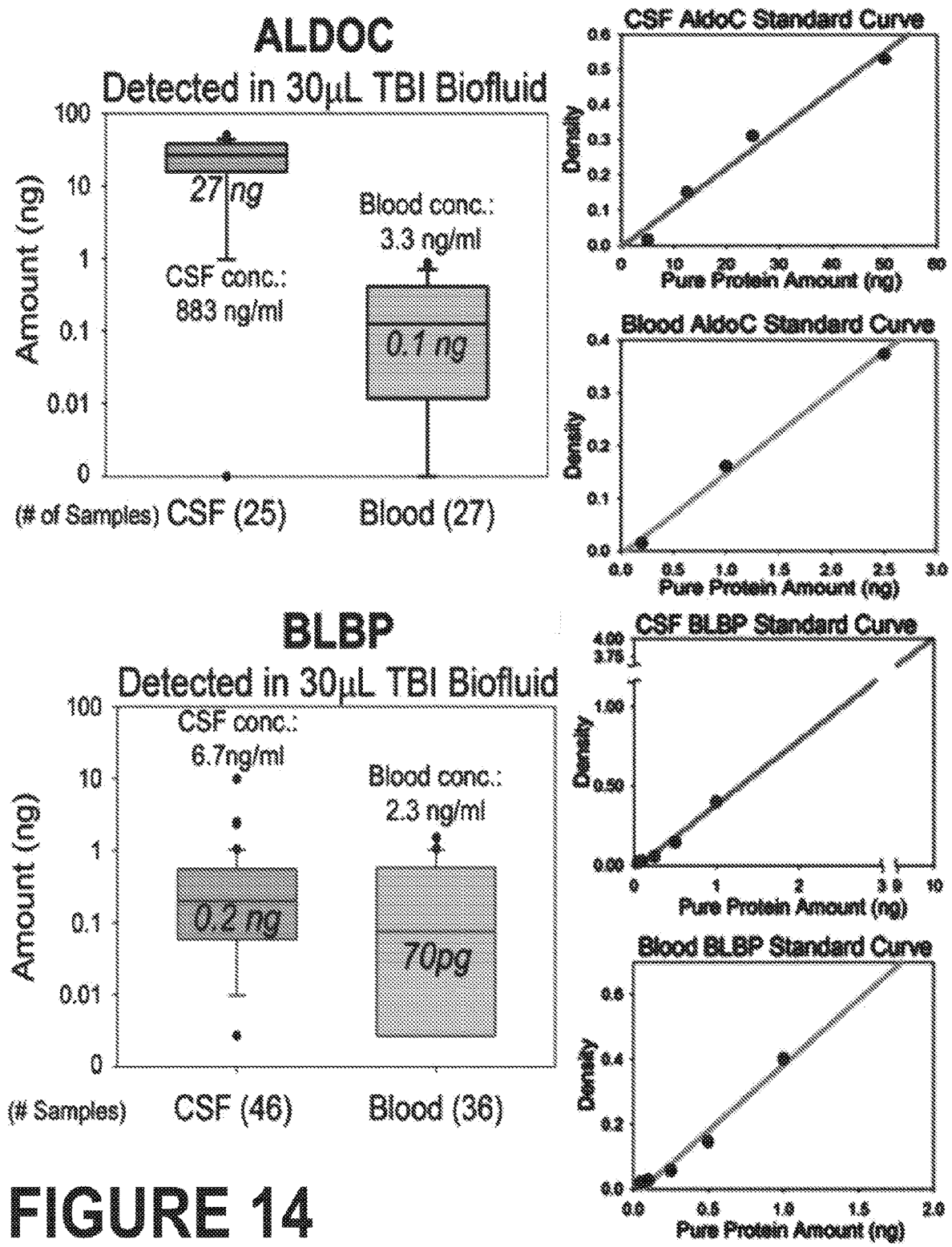
FIG. 14: Quantitative antibody-based evaluation of ALDOC and BLBP amounts and concentration ranges in TBI CSF and blood using known amounts of pure proteins.

This Example provides a quantitative antibody-based evaluation of ALDOC and BLBP levels in CSF and blood of TBI specimens using standard curves. Box plots in FIG. 14 show median and interquartile concentration ranges of ALDOC (left) and BLBP (right) and their amounts in CSF and blood (serum and plasma). Inserts show dose-response using known amounts of isoform-specific recombinant proteins ALDOC and BLBP using two concentration ranges and immunoblot detection conditions (see Table 7).

Figure 15:
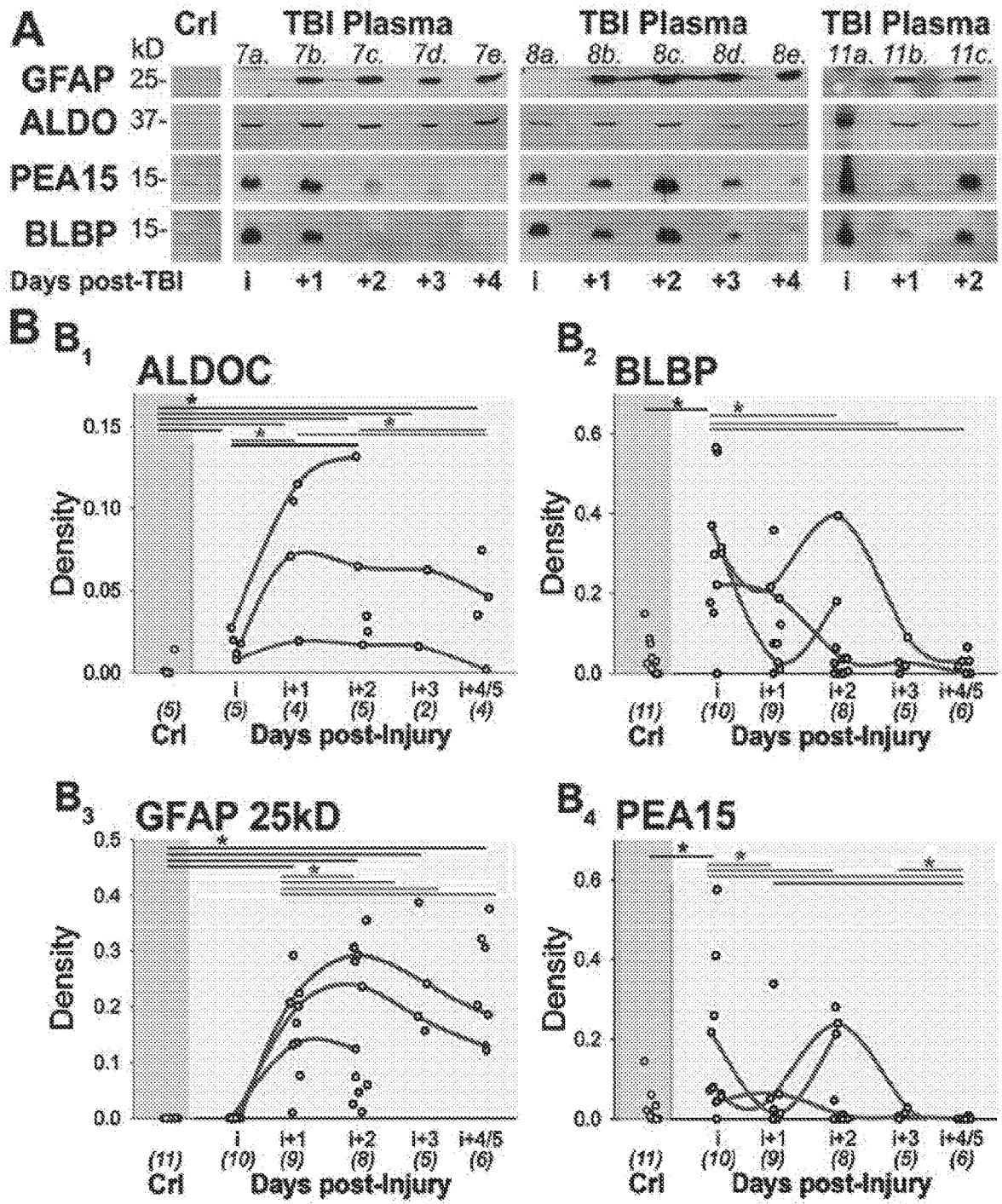
FIG. 15: Blood-compatible astroglial biomarkers in blood samples of severe TBI patients, as shown by immunoblots (A) and graphs of amount measured over time after injury (B).

Example 13: Detection of Astroglial Biomarkers in Blood Samples of Severe TBI Patients This Example demonstrates that the astroglial trauma markers are compatible with blood testing, using samples obtained from patients having severe TBI. FIG. 15A shows longitudinal plasma samples from 3 different severe TBI patients alongside one control plasma sample (Crl). Abundant proteins are removed using immunoaffinity albumin and immunoglobulin depletion columns (Sigma, ProteoPrep). New GFAP breakdown product of 25 kDa was never detected on injury day (i) but appeared on subsequent post-injury days. ALDOC was consistently present at all time points in all 3 patients. Short-lived markers PEA15 and BLBP were robustly present on injury day and showed different temporal profiles over subsequent days post-injury in each patient. Plotted in FIG. 15B are scaled densitometry signals for ALDOC (B1), BLBP (B2), GFAP/25 kDa BDP (B3) and PEA15 (B4) from 26 serum and 24 plasma samples derived from 22 severe TBI patients compared with up to 11 control blood samples (Crl). Longitudinal same patient data are connected by gray lines. ALDOC was significantly elevated on injury day and every post-injury day, while GFAP was significantly elevated beginning on the first post-injury day. BLBP and PEA15 had significant elevation on injury day versus control levels.

Example 14: Extended Detection Window of ALDOC Versus GFAP

Figure 16:
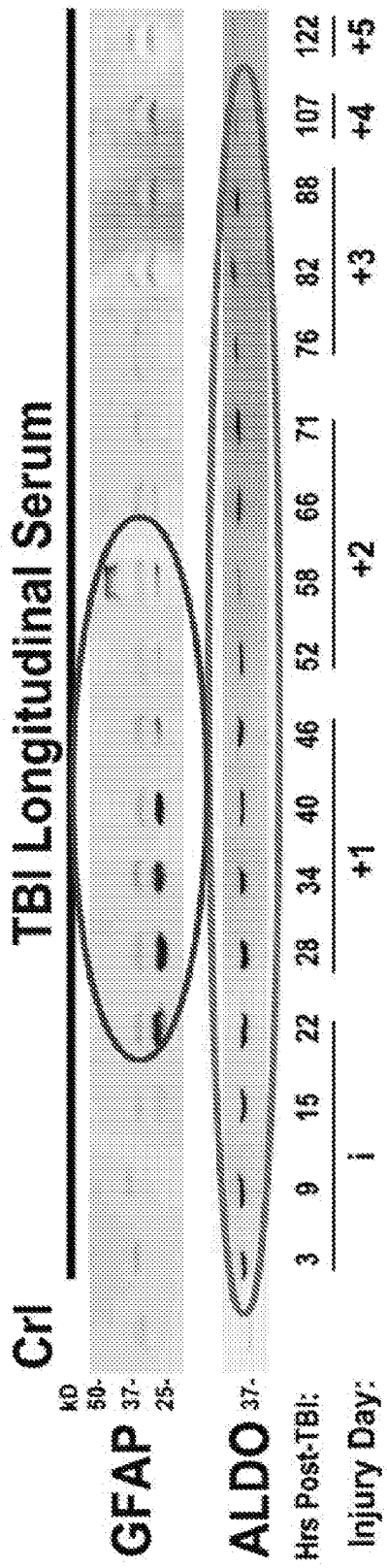
FIG. 16: Immunoblots of longitudinal severe TBI serum sample show extended detection window of ALDOC versus GFAP.

This Example demonstrates, using a longitudinal severe TBI serum sample, the extended detection window of ALDOC versus GFAP. ALDOC was detected 19 hours prior to first detection of GFAP 25 kDa BDP and ALDOC signals were present over two days beyond the last specific GFAP signal, a 37 kDa known GFAP BDP (FIG. 16).

Example 15: BLBP Breakdown Product

Figure 17:
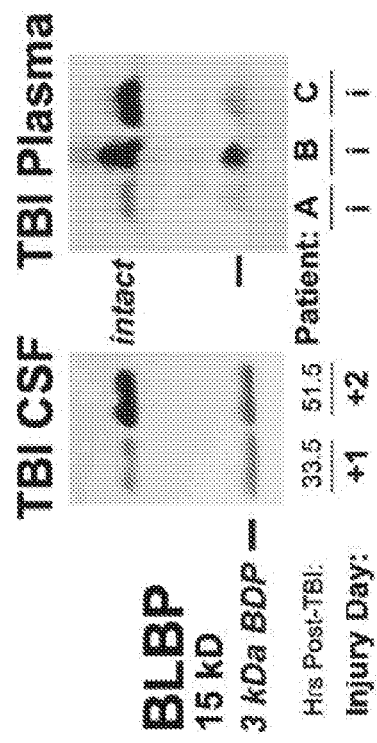
FIG. 17: Immunoblots showing BLBP breakdown product in CSF and plasma after TBI.

In addition to the full size, 15 kDa BLBP a 3 kDa BLBP-specific fragment was detected using 2 antibodies in TBI CSF and plasma on injury day and various post-injury days. Results are shown in FIG. 17.

Example 16: Acute Circulatory Appearance of TBI Markers

Figure 18:
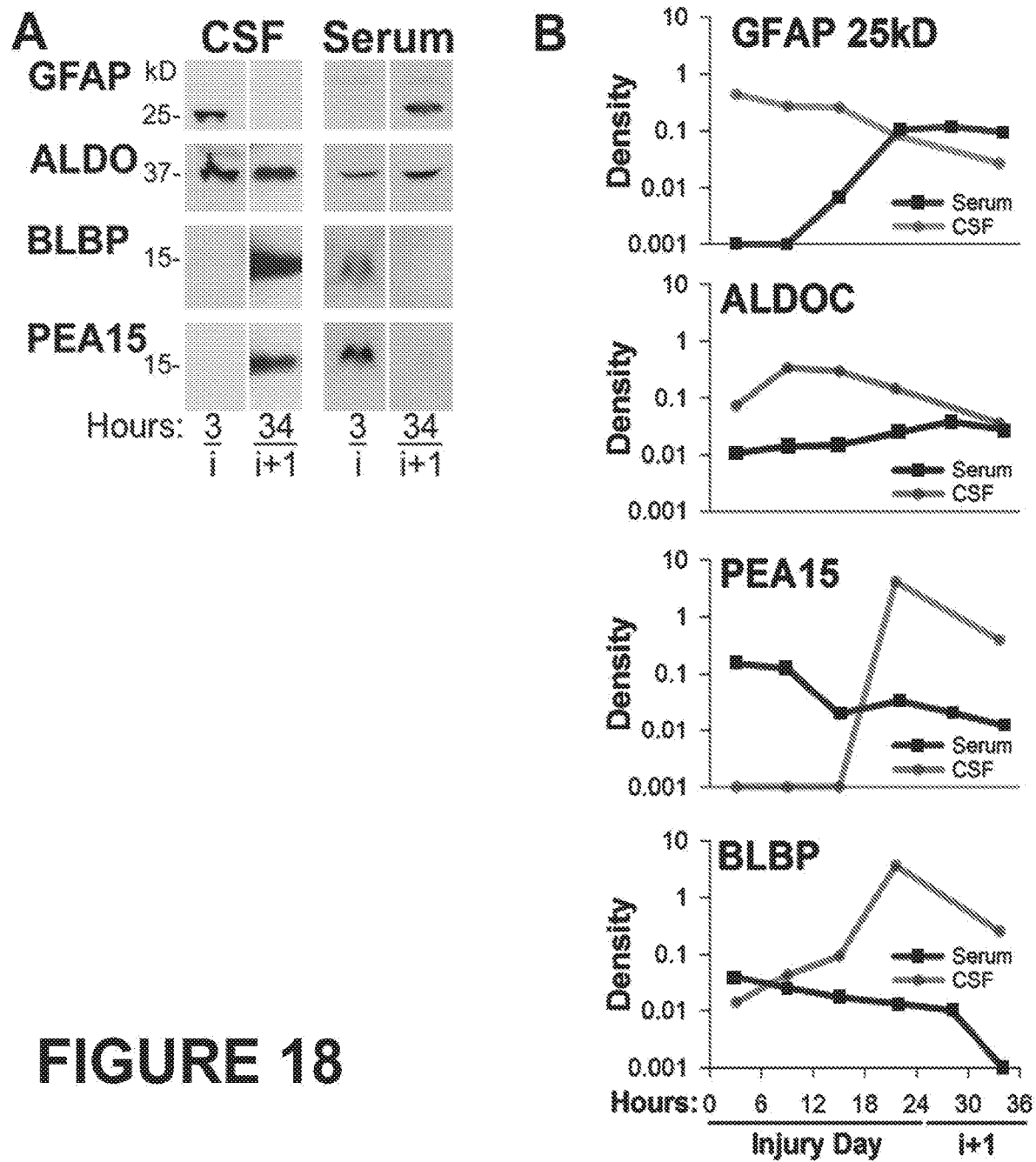
FIG. 18: Evidence for acute circulatory appearance of astroglial injury markers due to direct passage across damaged blood-brain barrier, as shown by immunoblots (A) and graphs of measured amounts over time after injury.

FIG. 18 presents evidence for acute circulatory appearance of new astroglial injury markers due to direct passage across damaged blood-brain barrier. Panel A of FIG. 18 shows immunoblots for GFAP 25 kDa BDP along with ALDOC, BLBP and PEA15 in CSF and serum of the same severe TBI patient acutely after TBI (3 hours post-injury), as well as on the first post-injury day. While GFAP appeared first in the CSF and with a day delay in serum, ALDOC was present in both biofluids at both time points. BLBP and PEA15 were first present in serum and appeared with delay in CSF. Traces on log-spaced axis of all 4 astroglial markers document the switch for GFAP 25 kDa BDP from CSF into serum, steadier presence of biofluid-stable ALDOC, and the presence of short-lived BLBP and PEA15 in serum prior to their appearance and delayed elevation in CSF (FIG. 18B).

These observations suggest the direct passage of ALDOC, BLBP and PEA15 from the injury site into the circulation. All three markers are localized in astroglial processes, with fine endings known to entirely wrap capillaries and blood vessels (Mathiisen et al., 2010). Traumatic injury, even mild TBI, causes rupture of perivascular astroglial fibers, allowing these markers a direct passage into the blood (Barzo et al., 1996; Hicks et al., 1993; Korn et al., 2005). GFAP is not localized in astroglial endings, and, as shown in FIG. 3, the 25 kDa GFAP BDP takes time to be generated, suggesting a delayed release during cell death leading to accumulation first in the CSF, and subsequent appearance in serum. Advantage of a direct passage of astroglial endfeet via open blood-brain barrier lays in enabling very acute post-injury blood-testing.

Figure 19:
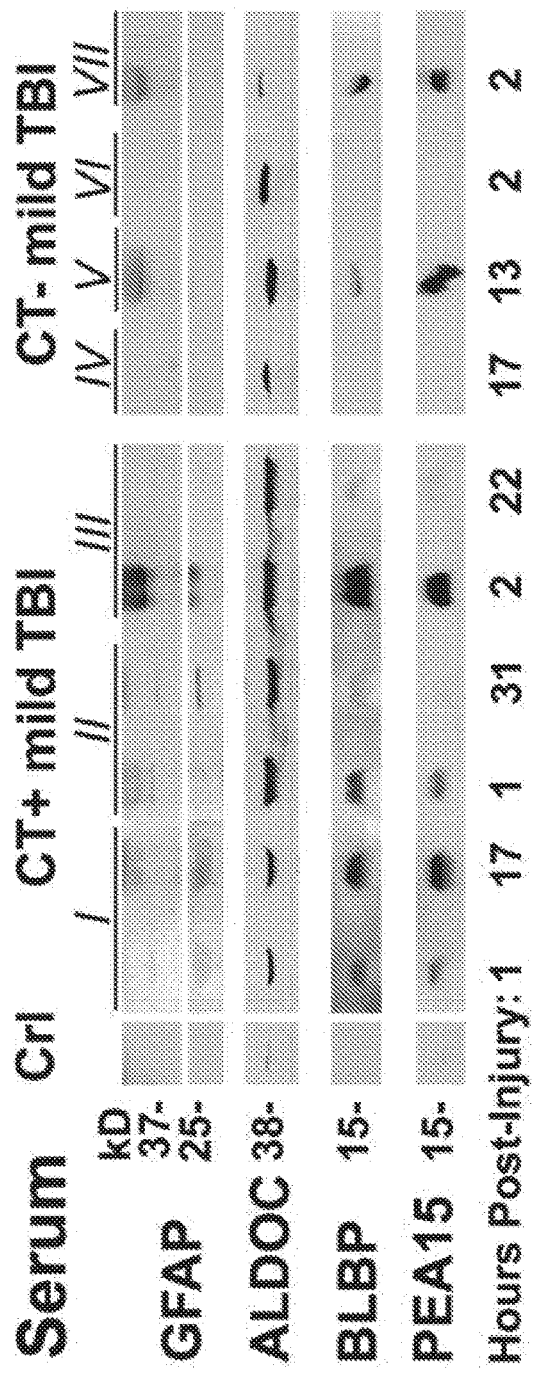
FIG. 19: Immunoblot data showing top tier astroglial injury markers and PEA15 are detected robustly and early in serum of mild TBI patients after concussions with or without complication (CT+: with complication—positive CAT scan; CT−: without complication, no CAT scan finding).

Example 17: Early Detection of Astroglial Injury Markers in Serum of Mild TBI Patients This Example demonstrates robust and early detection of top tier astroglial injury markers in serum of mild TBI patients. Shown in FIG. 19 are 10 serum samples from 7 mild TBI (mTBI) patients early after injury alongside of one control serum (Crl). Samples were probed for GFAP, ALDOC, BLBP and PEA15. Specific GFAP signals were faint and limited to 4 mTBI patients with one patient showing GFAP/25 kDa BDP by 31 hours post-injury (patient #II). ALDOC 38 kDa BDP was consistently and strongly elevated in all mTBI patients versus control. BLBP and PEA15 showed variable intensity and were present in 5 mTBI patients. ALDOC, BLBP and PEA15 were detected already one hour post-injury. Concussion patients received computed tomography (CT) scans and those with positive findings of a lesion/bleed were classified as CT+, potentially complicated mTBI patients, and those without visible wounds were CT-negative, or uncomplicated (Buki et al., 2015). Robust presence of ALDOC and differential signals for BLBP and PEA15 are suited to augment risk identification among concussion patients.

Example 18: Acute and Robust Detection of Serum ALDOC in Pediatric TBI

Figure 20:
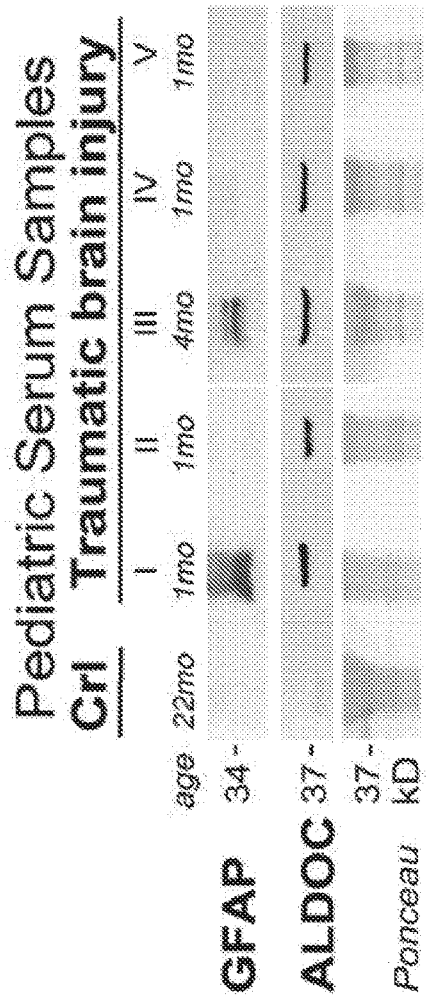
FIG. 20: Immunoblot data showing acute and robust detection of serum ALDOC in pediatric TBI, infants.

FIG. 20 shows acute and robust detection of ALDOC in pediatric TBI patient serum samples. Injury day serum samples from 5 infants (1-4 months of age) suffering TBI are shown next to a control serum from a child aged 22 months. Robust ALDOC signals are detected in all infant TBI versus control cases while only two infants showed weak GFAP signal (34 kDa BDP, not previously described, cases # I, III).

Example 19: ALDOC as a CSF Marker for Alzheimer's Disease

This Example demonstrates that CSF samples from patients afflicted with the chronic neurodegenerative condition of Alzheimer's disease exhibit equally distinct levels of full size (40 kDa) and 38 kDa BDP ALDOC. In contrast, ALDOC detected in CSF of an acute TBI patient shows a distinct preponderance of full size (40 kDa) versus 38 kDa BDP. Shown in FIG. 21 are 7 CSF samples from 5 Alzheimer's disease patients (AD, stage 0.5, cases #II and III; stage 1, cases # IV and V; based on Fagan et al., Science Transl. Med. 2014) compared to one severe TBI patient (case # I) and two age-matched controls (cases # VI and VII) and protein stain for loading (Ponceau S). The TBI patient had mainly full size ALDOC and little 38 kDa fragment on day 4 post-injury, while the chronic degenerative AD samples showed equal presence of full size and 38 kDa ALDOC BDP. The data suggest that acute and chronic brain injury can be distinguished on the basis of ALDOC/ALDOC BDP ratio.

TABLE 2

Distinction between TBI and Alzheimer's disease, using ratio between full size ALDOC and its 38 kDa proteolytic fragment in patients' CSF

|  | ALDOC 40 kD/38 kD All antibodies used | ALDOC 40 kD/38 kD Same antibody (E9) used |
|---|---|---|
| AD | 0.61 ± 0.25 | 0.42 ± 0.14 |
| TBI | 3.63 ± 3.26 | 8.56 ± 0.85 |
| AD v TBI | p = 0.0001 | p = 0.00002 |

The table shows average ratios of full size ALDOC (40 kDa) over its breakdown product (38 kDa) in CSF of Alzheimer's Disease (AD) patients and moderate to severe TBI patients. Different ALDOC antibodies to different epitopes of the protein resulted in varying emphasis of the 40 versus 38 kDa band signal intensities. On the left data of all ALDOC antibodies were combined averaging 20 AD samples and 25 TBI samples. The average AD ratio was 6 fold smaller than the average TBI ratio that was significant by two-tailed T-test. On the right 10 AD CSF samples and 5 TBI patient's samples were analyzed using same antibody (E9) for ALDOC detection. There was again a significant 20× difference between TBI, showing more full size signal and AD showing more BDP ALDOC signal. Data examples are shown in FIG. 21. This provides a distinction between TBI and chronic neurodegenerative disease. Both data selections result in significantly different ratios based on the increased abundance of the ALDOC major 38 kDa BDP signifying the chronic neurodegenerative condition. Acute TBI can easily be distinguished by a higher abundance of full size 40 kDa ALDOC acutely and up to 5 days post-TBI.

Example 20: Multivariate Discriminant Analysis

Multivariate Classification Tree Analysis (Breiman, 1984) was used to determine the markers that most accurately split the subject cohort into Control and Surviving or Non-surviving TBI patients on injury, analyzed by immunoblotting of 30 µl CSF sample each. Upon obtaining 100% accuracy with just two markers, AldoC and PTGDS (Table 3), the analysis was repeated allowing only those markers known to be detectable in the blood for future noninvasive assay (Table 4). Markers used for the data presented in Table 3 were Aldo C and PTGDS, while the markers considered, but not used, were: GFAP, PEA15, GFAP lower, S100B, BLBP, GS, APOB, PTGDS, and AldoC 38 kD. Table 3 thus summarizes the detection of TBI and survival outcome prediction using all markers in the classification tree analysis. This analysis selected ALDOC and PTGDS as the best partitioning markers. Among all inspected markers, those were utilized by the mathematical unsupervised learning approach. Groups, n=21, all Controls; and all injury day TBI of 30 TBI samples. The indicated 7 ng/30 µl CSF equals a concentration of 233 ng/ml CSF using immunoblotting. Accuracy was excellent, as grouping and predicted outcome match 100% correctly. FIG. 22 provides a partitioning illustration of the Table 3 thresholds.

TABLE 3

Detection of TBI and survival outcome prediction

| Group | n | Aldo C [OD] (ng/30ul CSF) | PTGDS [OD] | Prediction |
|---|---|---|---|---|
| A | 8 | >=0.078 (7 ng) | <0.174 or | TBI survivor (severe) |
| C |  | >=0.078 (7 ng) | >=0.202 | TBI survivor (moderate) |
| B | 2 | >=0.078 (7 ng) | 0.174 to 0.202 | TBI non-survivor |
| D | 11 | <0.078 (7 ng) | >0.202 | Control (healthy subject) |

Figure 23:
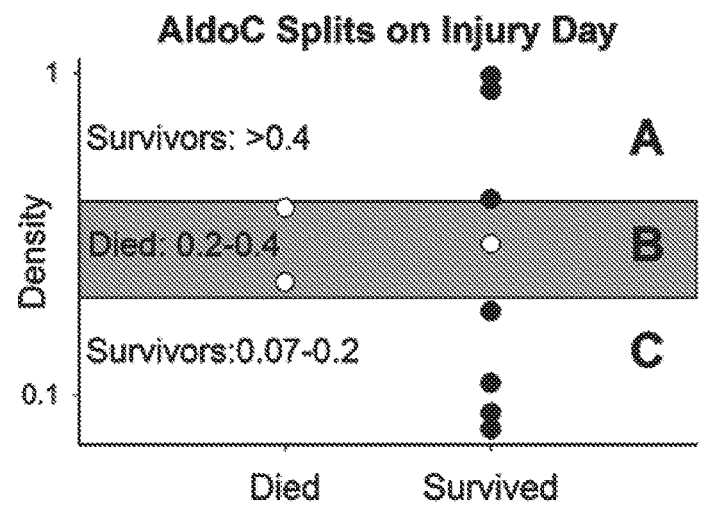
FIG. 23: Partitioning illustration of Table 4 thresholds.

Table 4 shows the detection of TBI and survival outcome prediction using the new blood-compatible glial markers. Markers used for Table 4 (1): Aldo C total. Markers considered but not used were: GFAP lower, BLBP, PEA 15, Aldo C 38 kD breakdown product (BDP). The markers NOT considered (omitted) were: GFAP total, S100B, GS, APOB, and PTGDS. Groups were: n=21 all Control; and injury day TBI patients of a total of 30 in entire cohort. Accuracy was 95%; the unweighted probability correct was 20/21, or 0.952. There was a 96% equal priority probability correct=0.96=(1.0+1.0+0.875). FIG. 23 provides a partitioning illustration of the Table 4 thresholds.

TABLE 4

Detection of TBI and survival outcome prediction using TBI markers

| Group | n | Aldo C total [OD] | Prediction |
|---|---|---|---|
| A | 4 | 0.078 to 0.22 | TBI survivor |
| B | 3 | 0.22 to 0.4 | TBI non-survivor |
| C | 3 | >=0.4 | TBI survivor |
| D | 11 | <0.078 | Control (healthy subject) |

Classification matrix for data in Table 4:

|  | Predicted-control | Predicted-died | Predicted-Survivor | total |
|---|---|---|---|---|
| True - control | 11 | 0 | 0 | 11 |
| True - died | 0 | 2 | 0 | 2 |
| True - survivor | 0 | 1 | 7 | 8 |

Receiver Operating Characteristic (applicable with higher n):

| Group | Area | N | N correct | Prop correct |
|---|---|---|---|---|
| Control | 1.0000 | 11 | 11 | 1.0 |
| Died | 0.9737 | 2 | 2 | 1.0 |
| survived | 0.9904 | 8 | 7 | 0.875 |

Example 21: Spearman Correlations Between Marker Signal Density [OD] and CAT Scan Imaging Data Secondary TBI progression can cause elevated intracranial pressure (ICP) which is often associated with secondary injury. Observed is a significant correlation between levels of cell death marker GFAP lower BDPs (19, 20, 25 kDa doublet) and ICP. Bleeding marker APOB is significantly correlated with extra+intraparenchymal lesion volume and midline shift. Both these CT findings are associated with brain bleeding, including epidural hematoma, subdural hematoma, subarachnoid hemorrhage and intraparenchymal lesions. Glial injury markers BLBP and PEA15, as well as cell death glial marker GFAP lower BDPs, are correlated with intraparenchymal lesions, including brain tissue contusion, intracranial hemorrhage and diffuse axonal injury.

Figure 24:
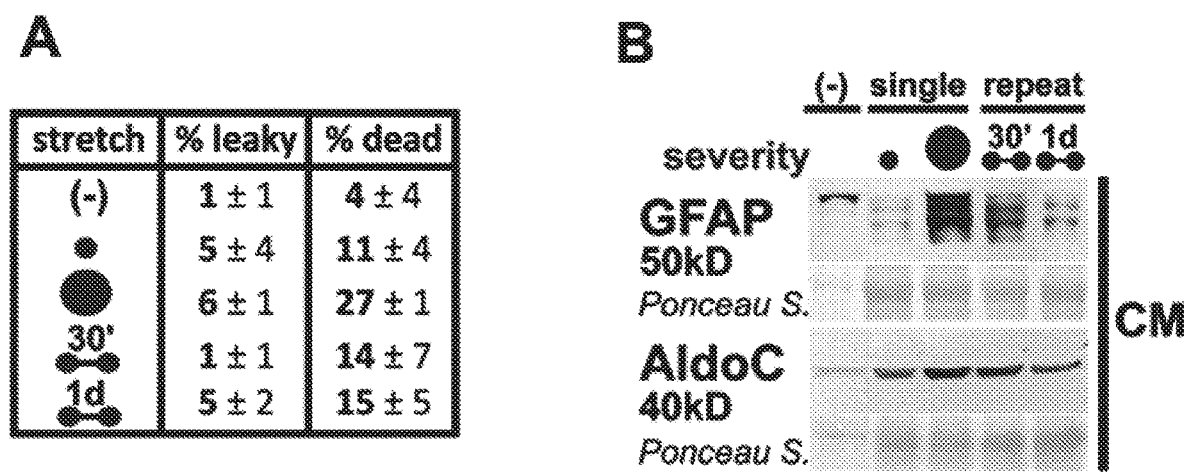
FIG. 24: Increased levels of glial trauma-release markers after repeated mild injury in the human trauma culture model, as indicated by percent astrocytes with acute membrane wounding and delayed cell death (A), and Conditioned medium (CM) levels of GFAP and AldoC after stretching (B).

Example 22: Increased Levels of Glial Trauma-Release Markers after Repeated Mild Injury in the Human Trauma Culture Model FIG. 24 shows results obtained using a model for repeat mild injury. Human astrocytes received a single (•) or double (•-•) mild pressure pulse 30 mins apart (30') or one day apart (1 D). Cell populations of acute leaky and delayed dead were not much changed by the repeated trauma (FIG. 24A). Yet, conditioned medium (CM) fluid levels of trauma-release markers GFAP and AldoC were elevated after shortly-followed repeated mild injury versus a single mild stretch, and were only slightly elevated when the two insults were one day apart. AldoC levels nearly reached those of a single severe insult (•) after shortly-followed mild stretches, indicating its sensitivity to repeated injury.

Figure 25:
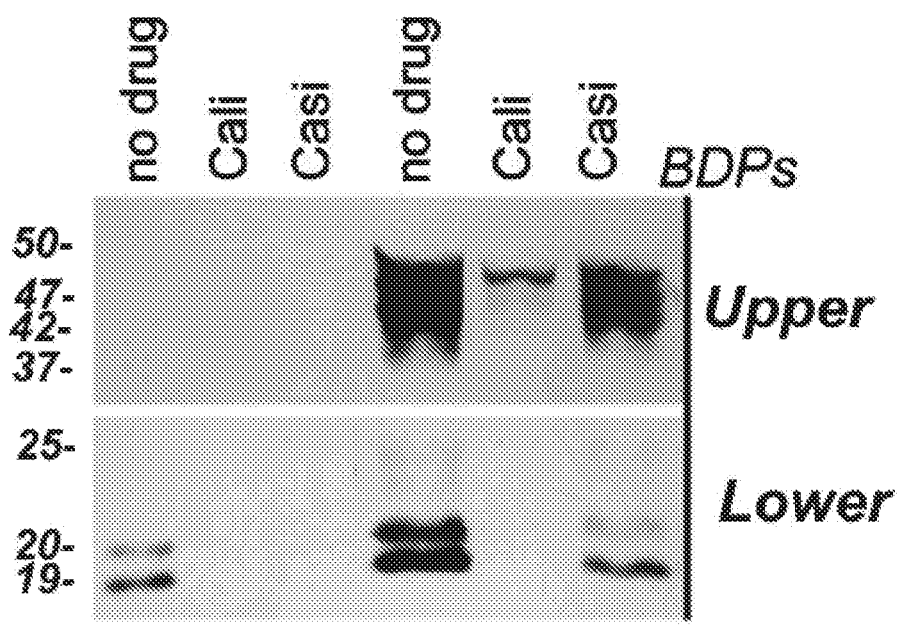
FIG. 25: Two film exposures of GFAP, showing that calpain and caspase activation generated GFAP upper and lower breakdown products after trauma.

Example 23: Calpain and Caspase Activation Generated GFAP Upper and Lower Breakdown Products after Trauma Shown in FIG. 25 are two film exposures of GFAP, upper and lower breakdown products 48 hour post-injury in conditioned medium samples using the DAKO anti-GFAP polyclonal antibody. Severely stretched and unstretched cultures received either no drug, calpain inhibitor PD150606 (100 µM, "Cali") or pan-caspase inhibitor Z-VAD FMK (8.8 µM, "Casi"). Trauma-released GFAP upper and lower BDPs were reduced by both calpain and caspase inhibition, suggesting trauma induced activation of both enzymes degrading GFAP after injury. Part of this enzymatic breakdown occurs in cells, part extracellular as suggested by similar analyses of cell lysate fractions of the same experiments. Minor release of lower GFAP BDPs in unstretched cultures was due to small numbers of non-traumatic cell death.

TABLE 5

Spearman Correlations between marker signal density and CAT scan data

| New TBI marker panel | ICP, Intracranial pressure | | Midline Shift (edema indication) | | Extra + Intra Parenchymal Lesion Volume | | Intra-parenchymal Lesion Volume | |
|---|---|---|---|---|---|---|---|---|
|  | Correlation | p-value | Correlation | p-value | Correlation | p-value | Correlation | p-value |
| Lower GFAP |  |  |  |  |  |  |  |  |
| BDPs | 0.834 | 0.00059 | 0.121 | 0.733 | 0.676 | 0.136 | 0.775 | 0.333 |
| ALDOC | −0.165 | 0.614 | −0.0872 | 0.776 | −0.126 | 0.72 | −0.4 | 0.517 |
| BLBP | 0.204 | 0.559 | −0.194 | 0.58 | 0.116 | 0.803 | 0.6 | 0.417 |
| PEA15 | 0.21 | 0.55 | 0.373 | 0.321 | 0.667 | 0.233 | 0.738 | 0.333 |
| APOB | −0.258 | 0.446 | 0.684 | 0.0361 | 0.986 | 0.0028 | 0.667 | 0.233 |

Example 24: Antibodies and Proteins Used for Western Blotting of Astroglial Injury Markers

TABLE 6

Antibodies and proteins used for western blotting of markers

| Name | Antibodies, recombinant proteins | Epitope | Comments |
|---|---|---|---|
| GFAP | Rabbit polyclonal anti-GFAP (DAKO, Z0334) | Whole cow GFAP | Polyclonal Abs recognize full size GFAP, upper & lower BDP set |
|  | Chicken polyclonal anti GFAP (ThermoFisher Scientific, PA1-10004) | Whole bovine GFAP |  |
| ALDOC | Rabbit affinity purified polyclonal anti-ALDOC (Genetex, GTX102284) | Recombinant ALDOC fragment amino acids 10-163 (P09972) |  |
|  | Rabbit Serum 88, 89 (EnCor, Biotech) | Recombinant whole ALDOC, BDPs |  |
|  | Several monoclonal ALDOC antibodies (EnCor): IgG1 mab 1A1 (MCA-1A1), IgG1 mab E9 (MCA-E9), IgG1 mab 4A9 (MCA-4A9), IgG1 mab 5C9 (still under development) Standard: His-tagged human ALDOC recombinant protein (EnCor Biotech. Inc.) | Mab 1A1: C-terminal peptide, does not detect ALDOC BDPs, no signal in blood; Mab E9: Recombinant whole ALDOC, detects ALDOC BDPs, signal in human blood (serum, plasma); Mab 4A9: N-terminal peptide sequence: MPHSYPALSAEQKKELS (SEQ ID NO: 1), signal in human and pig blood); Mab 5C9: N-terminus, signal in human blood (serum & plasma). | Standard curves using pure recombinant ALDOC (EnCor) See FIG. 14 |
| GS | Rabbit IgG fraction polyclonal anti GS (Sigma, G2781) | GS peptide amino acids 357-373, BDPs are seen, more sensitive |  |
|  | Mouse mab IgG2A to GS clone 6 (BD Transduction, 610517) | Full size GS, less sensitive no BDPs |  |
| PEA15 | Rabbit polyclonal affinity purified anti PEA15 (Cell Signaling) Standard: Recombinant PEA15 (EnCor) | Human PEA15 peptide surrounding Leu60 |  |
| BLBP = FABP7 = B-FABP | Affinity purified rabbit polyclonal anti-FABP7 (Millipore) | GST-tagged recombinant full size human FABP7, brain specific (Millipore) | Standard curves using pure recombinant BLBP (EnCor) see FIG. 14 |
|  | Affinity purified rabbit polyclonal anti-FABP7 clone RB22973(Abgent) | C-terminal human FABP7 peptide amino acids 104-132, brain specific (Abgent) |  |
|  | Mouse monoclonal IgG2b anti-FABP7 (Hycult, HM2299) Standard: His-tagged recombinant BLBP protein (EnCor Biotech. Inc.) | Peptide derived from human B-FABP sequence (Hycult) |  |
| CRYAB = HSP27 | Mouse monoclonal IgG1 anti-CRYAB (Enzo, 1B61-3G4) | Whole bovine CRYAB, recognizes full size and BDPs |  |
|  | Rabbit affinity purified polyclonal anti-CRYAB (EMD Millipore, ABN185) | N-terminus |  |
| APOB | Rabbit affinity purified polyclonal IgG anti-APOB (PTGlab, 20578-1-AP) | Unspecified APOB peptide APOB 120-130 kDa observed band, full size 516 kDa |  |
| PTGDS | Rabbit affinity purified IgG anti-PTGDS (USBiological, P9053-24D) | Synthetic human PTGDS peptide amino acids 120-190 |  |

Example 25: Multiple Reaction Monitoring Mass Spectrometry

Biofluid concentrations of the TBI injury biomarker proteins were measured by targeted multiple-reaction-monitoring (MRM) mass spectrometry. Biofluid samples were first digested using endoproteinase trypsin, cleaving all proteins into their respective tryptic peptides. Protein specific peptide signals were used as a surrogate measure for their respective proteins. In MRM-MS, peptide signals are measured by what are known as precursor→to product ion transitions as shown in Table 7 below (e.g. 554.821 (2+)→924.514 (1+, y8)). Selection of specific precursor ions of interest allows for increased sensitivity. By measuring signal from specific product ions from selected precursors, MRM allows for a high degree of analyte specificity. For quantitation, defined amounts of stable isotope-labeled standard (SIS) peptides containing either a heavy lysine [K(Label:13C(6)15N(2))] or heavy arginine [R(Label:13C(6)15N(4))] are spiked into biofluid samples. These heavy standard peptides are chemically identical to their endogenous (light) counterparts but display a mass shift of +8 and +10 Da (K and R respectively) for differentiation from endogenous biofluid peptides. Comparison of the peak area ratios between the light and heavy MRM transitions allows for absolute quantitation of biomarker concentrations. For our assay, trypsin digested biofluids were first separated by reversed phase liquid chromatography using a 0.1% formic acid in water and 0.1% formic acid in acetonitrile elution system to further reduce sample complexity and improve signal sensitivity.

TABLE 7

Multiple Reaction Monitoring mass spectrometry peptide TBI biomarkers

| Name | Peptide Sequence | Measured MRM Transition |
|---|---|---|
| GFAP all within core fragment | ALLAAELNQLR (Heavy) SEQ ID NO: 2 ALLAAELNQLR (Light) SEQ ID NO: 2 LADVYQAELR (Heavy) SEQ ID NO: 3 LADVYQAELR (Light) SEQ ID NO: 3 | 554.821 (2+) → 924.514 (+1, y8) 554.821 (2+) → 853.477 (+1, y7) 554.821 (2+) → 782.439 (+1, y6) 549.816 (2+) → 914.505 (+1, y8) 549.816 (2+) → 843.468 (+1, y8) 549.816 (2+) → 722.431 (+1, y8) 594.758 (2+) → 1003.508 (+1, y8) 594.758 (2+) → 789.413 (+1, y6) 594.758 (2+) → 626.350 (+1, y5) 589.314 (2+) → 993.500 (+1, y8) 589.314 (2+) → 779.408 (+1, y6) 589.314 (2+) → 616.341 (+1, y5) |
| ALDOC | TPSALAILENANVLAR (Heavy) SEQ ID NO: 4 TPSALAILENANVLAR (Light) SEQ ID NO: 4 LSQIGVENTEENR (Heavy) SEQ ID NO: 5 LSQIGVENTEENR (Light) SEQ ID NO: 5 | 831.974 (2+) → 1193.688 (+1, y11) 831.974 (2+) → 1122.651 (+1, y10) 831.974 (2+) → 1009.566 (+1, y9) 826.970 (2+) → 1183.679 (+1, y11) 826.970 (2+) → 1112.642 (+1, y10) 826.970 (2+) → 999.558 (+1, y9) 749.872 (2+) → 1170.563 (+1, y10) 749.872 (2+) → 1057.478 (+1, y9) 749.872 (2+) → 901.389 (+1, y7) 744.868 (2+) → 1160.554 (+1, y10) 744.868 (2+) → 1047.470 (+1, y9) 744.868 (2+) → 891.380 (+1, y7) |
| GS | DIVEAHYR (Heavy) SEQ ID NO: 6 DIVEAHYR (Light) SEQ ID NO: 6 | 506.758 (2+) → 784.398 (+1, y6) 506.758 (2+) → 685.329 (+1, y5) 506.758 (2+) → 556.287 (+1, y4) 501.753 (2+) → 774.389 (+1, y6) 501.753 (2+) → 675.321 (+1, y5) 501.753 (2+) → 546.278 (+1, y4) |
| PEA15 | DNLSYIEHIFEISR (Heavy) SEQ ID NO: 7 DNLSYIEHIFEISR (Light) SEQ ID NO: 7 | 582.629 (3+) → 661.354 (+1, y5) 582.629 (3+) → 702.363 (+2, y11) 582.629 (3+) → 658.847 (+2, y10) 579.293 (3+) → 651.346 (+1, y5) 579.293 (3+) → 697.359 (+2, y11) 579.293 (3+) → 653.843 (+2, y10) |
| BLBP = FABP7 | ALGVGFATR (Heavy) SEQ ID NO: 8 ALGVGFATR (Light) SEQ ID NO: 8 | 451.260 (2+) → 717.392 (+1, y7) 451.260 (2+) → 660.370 (+1, y6) 451.260 (2+) → 561.302 (+1, y5) 446.256 (2+) → 707.384 (+1, y7) 446.256 (2+) → 650.362 (+1, y6) 446.256 (2+) → 551.294 (+1, y5) |
| CRYAB = HSP 27 | HFSPEELK (Heavy) SEQ ID NO: 9 HFSPEELK (Light) SEQ ID NO: 9 | 497.758 (2+) → 857.450 (+1, y7) 497.758 (2+) → 710.381 (+1, y6) 497.758 (2+) → 623.349 (+1, y5) 493.751 (2+) → 849.435 (+1, y7) 493.751 (2+) → 702.367 (+1, y6) 493.751 (2+) → 615.335 (+1, y5) |
| APOB | SPAFTDLHLR (Heavy) SEQ ID NO: 10 SPAFTDLHLR (Light) SEQ ID NO: 10 | 389.545 (3+) → 764.429 (+1, y6) 389.545 (3+) → 663.381 (+1, y5) 389.545 (3+) → 491.771 (+2, y8) 386.208 (3+) → 754.421 (+1, y6) 386.208 (3+) → 653.373 (+1, y5) 386.208 (3+) → 486.767 (+2, y8) |
| PTGDS | APEAQVSVQPNFQQDK (Heavy) SEQ ID NO: 11 APEAQVSVQPNFQQDK (Light) SEQ ID NO: 11 | 897.449 (2+) → 1297.663 (+1, y11) 897.449 (2+) → 1198.594 (+1, y10) 897.449 (2+) → 884.435 (+1, y7) 893.442 (2+) → 1289.648 (+1, y11) 893.442 (2+) → 1190.580 (+1, y10) 893.442 (2+) → 876.421 (+1, y7) |

REFERENCES

Barbee, K. A. 2005. Mechanical cell injury. *Ann N Y Acad Sci.* 1066:67-84.

Barzo, P., et al. 1996. Magnetic resonance imaging-monitored acute blood-brain barrier changes in experimental traumatic brain injury. *Journal of neurosurgery.* 85:1113-1121.

Breiman, L. 1984. Classification and regression trees. Wadsworth International Group, Belmont, Calif. x, 358 p. pp.

Buki, A., et al. 2015. Minor and repetitive head injury. *Advances and technical standards in neurosurgery.* 42:147-192.

Cahoy, J. D., et al. A transcriptome database for astrocytes, neurons, and oligodendrocytes: a new resource for understanding brain development and function. *The Journal of neuroscience: the official journal of the Society for Neuroscience.* 28:264-278.

Crowder, M. J., and D. J. Hand. 1990. Analysis of repeated measures. In Monographs on statistics and applied probability. Chapman and Hall, London; New York. 1-59.

Fabrigar, L. R., and D. T. Wegener. 2012. Exploratory factor analysis. Oxford University Press, Oxford; New York. viii, 159 p. pp.

Hicks, R. R., et al. 1993. Mild experimental brain injury in the rat induces cognitive deficits associated with regional neuronal loss in the hippocampus. *Journal of neurotrauma.* 10:405-414.

Korn, A., et al. 2005. Focal cortical dysfunction and blood-brain barrier disruption in patients with Postconcussion syndrome. *J Clin Neurophysiol.* 22:1-9.

Lee, J. H., et al. 2013. A novel porcine model of traumatic thoracic spinal cord injury. *Journal of neurotrauma.* 30:142-159.

Levine, J., et al. 2016. Traumatically injured astrocytes release a proteomic signature modulated by STAT3-dependent cell survival. *Glia.* 64:668-694.

Levine, J., et al. 2015. Traumatically injured astrocytes release a proteomic signature modulated by STAT3 dependent cell survival. *Glia.* online.

Mathiisen, T. M., et al. 2010. The perivascular astroglial sheath provides a complete covering of the brain microvessels: an electron microscopic 3D reconstruction. *Glia.* 58:1094-1103.

Omenn, G. S., et al. 2005. Overview of the HUPO Plasma Proteome Project: results from the pilot phase with 35 collaborating laboratories and multiple analytical groups, generating a core dataset of 3020 proteins and a publicly-available database. *Proteomics.* 5:3226-3245.

Schenk, S., et al. 2008. A high confidence, manually validated human blood plasma protein reference set *BMC Med Genomics.* 1:41.

Sondej, M., et al. 2011. Sample preparation of primary astrocyte cellular and released proteins for 2-D gel electrophoresis and protein identification by mass spectrometry. In Sample preparation in biological mass spectrometry. Vol. 39. A. Ivanov and A. Lazarev, editors. Springer, Dordrecht 829-849.

Tucker, L. M., RC. 1997. Exploratory Factor Analysis. University of Illinois; Ohio State University.

Wanner, I. B. 2012. An in vitro trauma model to study rodent and human astrocyte reactivity. *Methods in molecular biology.* 814:189-219.

Throughout this application various publications are referenced. The disclosures of these publications in their entireties are hereby incorporated by reference into this application in order to describe more fully the state of the art to which this invention pertains.

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended claims.

What is claimed is:

1. A method for detection and treatment of traumatic brain injury (TBI) in a subject, the method comprising:
   (a) contacting a specimen of bodily fluid obtained from the subject with reagents for assaying for a marker of TBI, wherein the marker of TBI comprises aldolase C (ALDOC), or a trauma-specific break down product (BDP) of ALDOC, wherein the trauma-specific BDP of ALDOC is selected from the group consisting of a 38 kDa fragment, a 35 kDa fragment, a 30 kDa fragment, and a 23 kDa fragment;
   (b) measuring the amount of marker present in the specimen as compared to a control sample;
   (c) determining the presence of an elevated amount of the marker in the specimen compared to the control sample; and
   (d) treating the subject for TBI when the specimen is determined to have an elevated amount of the marker.

2. The method of claim 1, wherein the marker of TBI further comprises brain lipid binding protein (BLBP/FABP7) or a BDP thereof.

3. The method of claim 1, further comprising measuring the amount of glutamine synthetase (GS), astrocytic phosphoprotein PEA-15 (PEA15), αB-crystallin (CRYAB/HSP27), a trauma-specific proteolytic cleavage product of GS, PEA15, or CRYAB, or any combination of two or more thereof, wherein the trauma-specific proteolytic cleavage product of GS is selected from the group consisting of a 37+35 kDa doublet, a 32 kDa fragment, a 23 kDa fragment, a 20 kDa fragment, and 18 kDa fragment; the trauma-specific proteolytic cleavage product of PEA15 is selected from the group consisting of a 12+13 kDa doublet and an 8 kDa fragment; and the trauma-specific proteolytic cleavage product of αB-crystallin is selected from the group consisting of an 18+19 kDa doublet, a 17 kDa fragment, a 15+14 kDa doublet and a 8 kDa fragment.

4. The method of claim 1, further comprising measuring the amount of apolipoprotein B (APOB) in a cerebrospinal fluid (CSF) sample obtained from the subject.

5. The method of claim 1, further comprising measuring the amount of a 20-30 kDa BDP of glial fibrillary acid protein (GFAP).

6. The method of claim 1, wherein the reagents of step (a) comprise antibodies that specifically bind the marker of TBI, and the measuring comprises immunoassay.

7. The method of claim 6, wherein the immunoassay comprises western blotting, immunofluorescence, immunoluminescence, radioimmunoassay, or enzyme linked immuno-sorbent assay (ELISA).

8. The method of claim 1, wherein the control sample is a pre-injury sample obtained from the subject.

9. The method of claim 1, wherein the control sample is an average value obtained from a control cohort of healthy subjects.

10. The method of claim 5, wherein no more than 4 markers are assayed.

11. The method of claim 1, wherein the specimen of bodily fluid comprises plasma, serum, cerebrospinal fluid (CSF), nasal fluid, cerumen, urine, saliva, lacrimal tears, or brain microdialysate.

12. The method of claim 1, wherein the reagents comprise protein-sequence and -fragment-specific peptides, and wherein the measuring comprises targeted quantitative mass spectrometry.

13. The method of claim 1, wherein the measuring comprises multiple or parallel reaction monitoring mass spectrometry.

14. The method of claim 1, wherein the subject has had a suspected injury, and the measuring is performed within 24 hours of a suspected injury to the subject.

15. The method of claim 1, wherein the subject has had a suspected injury, and the measuring is performed within one week of a suspected injury to the subject.

16. A method for monitoring treatment of traumatic brain injury (TBI) in a subject, the method comprising:
   (a) assaying a specimen of bodily fluid obtained from the subject being treated for TBI for a marker of TBI, wherein the marker of TBI comprises aldolase C (ALDOC), or a trauma-specific break down product (BDP) of ALDOC, wherein the trauma-specific BDP of ALDOC is selected from the group consisting of a 38 kDa fragment, a 35 kDa fragment, a 30 kDa fragment, and a 23 kDa fragment;
   (b) measuring the amount of marker present in the specimen as compared to a control sample; and
   (c) determining the presence of an elevated amount of the marker in the specimen compared to the control sample, thereby detecting progression of TBI in the subject; and
   (d) re-initiating or increasing treatment for TBI when the specimen is determined to have an elevated amount of the marker.

17. The method of claim 16, wherein the marker of TBI further comprises brain lipid binding protein (BLBP/FABP7) or a BDP thereof.

18. The method of claim 16, further comprising measuring the amount of glutamine synthetase (GS), astrocytic phosphoprotein PEA-15 (PEA15), αB-crystallin (CRYAB/HSP27), a trauma-specific proteolytic cleavage product of GS, PEA15, or CRYAB, or any combination of two or more thereof, wherein the trauma-specific proteolytic cleavage product of GS is selected from the group consisting of a 37+35 kDa doublet, a 32 kDa fragment, a 23 kDa fragment, a 20 kDa fragment, and 18 kDa fragment; the trauma-specific proteolytic cleavage product of PEA15 is selected from the group consisting of a 12+13 kDa doublet and an 8 kDa fragment; and the trauma-specific proteolytic cleavage product of αB-crystallin is selected from the group consisting of an 18+19 kDa doublet, a 17 kDa fragment, a 15+14 kDa doublet and a 8 kDa fragment.

19. The method of claim 16, further comprising measuring the amount of apolipoprotein B (APOB) in a cerebrospinal fluid (CSF) sample obtained from the subject.

20. The method of claim 16, further comprising measuring the amount of a 20-30 kDa BDP of glial fibrillary acid protein (GFAP).

21. The method of claim 16, wherein the measuring comprises immunoassay.

22. The method of claim 21, wherein the immunoassay comprises western blotting, immunofluorescence, immunoluminescence, radioimmunoassay, or enzyme linked immuno-sorbent assay (ELISA).

23. The method of claim 16, wherein the control sample is a pre-injury sample obtained from the subject.

24. The method of claim 16, wherein the control sample is an average value obtained from a control cohort of healthy subjects.

25. The method of claim 16, wherein no more than 4 markers are assayed.

\* \* \* \* \*

SEQUENCE LISTING

```
<160> NUMBER OF SEQ ID NOS: 11

<210> SEQ ID NO 1
<211> LENGTH: 17
<212> TYPE: PRT
<213> ORGANISM: Artificial Sequence
<220> FEATURE:
<223> OTHER INFORMATION: Mab 4A9: N-terminal peptide sequence

<400> SEQUENCE: 1

Met Pro His Ser Tyr Pro Ala Leu Ser Ala Glu Gln Lys Lys Glu Leu
1               5                   10                  15

Ser

<210> SEQ ID NO 2
<211> LENGTH: 10
<212> TYPE: PRT
<213> ORGANISM: Homo sapiens

<400> SEQUENCE: 2

Ala Leu Ala Ala Glu Leu Asn Gln Leu Arg
1               5                   10

<210> SEQ ID NO 3
<211> LENGTH: 10
<212> TYPE: PRT
<213> ORGANISM: Homo sapiens

<400> SEQUENCE: 3

Leu Ala Asp Val Tyr Gln Ala Glu Leu Arg
```

```
1               5                   10
```

<210> SEQ ID NO 4
<211> LENGTH: 16
<212> TYPE: PRT
<213> ORGANISM: Homo sapiens

<400> SEQUENCE: 4

```
Thr Pro Ser Ala Leu Ala Ile Leu Glu Asn Ala Asn Val Leu Ala Arg
1               5                   10                  15
```

<210> SEQ ID NO 5
<211> LENGTH: 13
<212> TYPE: PRT
<213> ORGANISM: Homo sapiens

<400> SEQUENCE: 5

```
Leu Ser Gln Ile Gly Val Glu Asn Thr Glu Glu Asn Arg
1               5                   10
```

<210> SEQ ID NO 6
<211> LENGTH: 8
<212> TYPE: PRT
<213> ORGANISM: Homo sapiens

<400> SEQUENCE: 6

```
Asp Ile Val Glu Ala His Tyr Arg
1               5
```

<210> SEQ ID NO 7
<211> LENGTH: 14
<212> TYPE: PRT
<213> ORGANISM: Homo sapiens

<400> SEQUENCE: 7

```
Asp Asn Leu Ser Tyr Ile Glu His Ile Phe Glu Ile Ser Arg
1               5                   10
```

<210> SEQ ID NO 8
<211> LENGTH: 9
<212> TYPE: PRT
<213> ORGANISM: Homo sapiens

<400> SEQUENCE: 8

```
Ala Leu Gly Val Gly Phe Ala Thr Arg
1               5
```

<210> SEQ ID NO 9
<211> LENGTH: 8
<212> TYPE: PRT
<213> ORGANISM: Homo sapiens

<400> SEQUENCE: 9

```
His Phe Ser Pro Glu Glu Leu Lys
1               5
```

<210> SEQ ID NO 10
<211> LENGTH: 10
<212> TYPE: PRT
<213> ORGANISM: Homo sapiens

<400> SEQUENCE: 10

```
Ser Pro Ala Phe Thr Asp Leu His Leu Arg
1               5                   10
```

```
<210> SEQ ID NO 11
<211> LENGTH: 16
<212> TYPE: PRT
<213> ORGANISM: Homo sapiens

<400> SEQUENCE: 11

Ala Pro Glu Ala Gln Val Ser Val Gln Pro Asn Phe Gln Gln Asp Lys
1               5                   10                  15
```